US011717303B2

(12) United States Patent
Kaplan et al.

(10) Patent No.: US 11,717,303 B2
(45) Date of Patent: Aug. 8, 2023

(54) DEVICES AND METHODS FOR EXCLUDING THE LEFT ATRIAL APPENDAGE

(71) Applicant: Conformal Medical, Inc., Merrimack, NH (US)

(72) Inventors: Aaron V. Kaplan, Norwich, VT (US); David Melanson, Hudson, NH (US); Carol Devellian, Topsfield, MA (US); Andy H. Levine, Newton, MA (US)

(73) Assignee: CONFORMAL MEDICAL, INC., Nashua, NH (US)

( * ) Notice: Subject to any disclaimer, the term of this patent is extended or adjusted under 35 U.S.C. 154(b) by 459 days.

(21) Appl. No.: 15/703,129

(22) Filed: Sep. 13, 2017

(65) Prior Publication Data

US 2018/0000490 A1 Jan. 4, 2018

Related U.S. Application Data

(63) Continuation of application No. 14/203,187, filed on Mar. 10, 2014, now Pat. No. 9,943,315.

(Continued)

(51) Int. Cl.
*A61B 17/12* (2006.01)
*A61B 17/00* (2006.01)
(Continued)

(52) U.S. Cl.
CPC .... *A61B 17/12181* (2013.01); *A61B 17/1215* (2013.01); *A61B 17/12122* (2013.01);
(Continued)

(58) Field of Classification Search
CPC ........ A61B 17/12181; A61B 17/12122; A61B 17/12145; A61B 17/1215;
(Continued)

(56) References Cited

U.S. PATENT DOCUMENTS 3,063,453 A * 11/1962 Brecht ................ A61F 13/2085
604/377
3,712,305 A 1/1973 Wennerblom et al.
(Continued)

FOREIGN PATENT DOCUMENTS

CA 1341519 2/2007
CN 102088927 A 6/2011
(Continued)

OTHER PUBLICATIONS

International Search Report dated Jul. 10, 2019, in International Application No. PCT/US2019/29364.
(Continued)

*Primary Examiner* — Jing Rui Ou
(74) *Attorney, Agent, or Firm* — Knobbe, Martens, Olson & Bear LLP

(57) ABSTRACT

Devices and methods for occluding the left atrial appendage (LAA) to prevent blood from clotting within the LAA and subsequently embolizing, particularly in patients with atrial fibrillation. A foam implant encapsulated with a tough thromboresistent membrane is placed via transvascular means into the LAA and anchored with adhesives and/or mechanical anchors. Tissue over- and in-growth are optimized to anchor the implant in place and provide a permanent occlusion.

16 Claims, 21 Drawing Sheets

Related U.S. Application Data

(60) Provisional application No. 61/779,802, filed on Mar. 13, 2013.

(51) Int. Cl.
    *A61B 17/22* (2006.01)
    *A61B 90/00* (2016.01)

(52) U.S. Cl.
    CPC .. *A61B 17/12145* (2013.01); *A61B 17/12159* (2013.01); *A61B 17/12172* (2013.01); *A61B 17/12177* (2013.01); *A61B 17/00491* (2013.01); *A61B 17/12136* (2013.01); *A61B 2017/00495* (2013.01); *A61B 2017/1205* (2013.01); *A61B 2017/22038* (2013.01); *A61B 2017/22048* (2013.01); *A61B 2090/064* (2016.02)

(58) Field of Classification Search
    CPC ........ A61B 17/12159; A61B 17/12172; A61B 17/12177; A61B 2090/064; A61B 17/00491; A61B 17/12136; A61B 2017/00495; A61B 2017/1205; A61B 2017/22038; A61B 2017/22048; A61B 17/0057; A61B 17/12022; A61F 6/146; A61F 6/20
    See application file for complete search history.

(56) References Cited

U.S. PATENT DOCUMENTS

| | | |
|---|---|---|
| 3,812,856 A | 5/1974 | Duncan et al. |
| 3,978,855 A | 9/1976 | McRae et al. |
| 4,061,145 A | 12/1977 | DesMarais |
| 4,475,911 A | 10/1984 | Gellert |
| 5,192,301 A | 3/1993 | Kamiya et al. |
| 5,456,693 A | 10/1995 | Conston et al. |
| 5,634,936 A | 6/1997 | Linden et al. |
| 5,670,572 A | 9/1997 | Ott et al. |
| 5,725,568 A | 3/1998 | Hastings |
| 5,792,179 A | 8/1998 | Sideris |
| 5,823,198 A | 10/1998 | Jones et al. |
| 5,847,012 A | 12/1998 | Shalaby et al. |
| 5,848,040 A | 12/1998 | Tanaka |
| 5,861,003 A | 1/1999 | Latson et al. |
| 5,865,791 A | 2/1999 | Whayne et al. |
| 5,969,000 A | 10/1999 | Yang et al. |
| 5,968,091 A | 11/1999 | Pinchuk |
| 6,152,144 A | 11/2000 | Lesh et al. |
| 6,162,168 A | 12/2000 | Schweich et al. |
| 6,231,561 B1 | 5/2001 | Frazier et al. |
| 6,290,674 B1 | 9/2001 | Roue et al. |
| 6,398,758 B1 | 6/2002 | Jacobsen et al. |
| 6,408,981 B1 | 6/2002 | Smith et al. |
| 6,419,669 B1 | 7/2002 | Frazier et al. |
| 6,423,252 B1 | 7/2002 | Chun et al. |
| 6,436,088 B2 | 8/2002 | Frazier et al. |
| 6,447,539 B1 | 9/2002 | Nelson et al. |
| 6,458,100 B2 | 10/2002 | Roue et al. |
| 6,551,303 B1 | 4/2003 | VanTassel et al. |
| 6,623,450 B1 | 9/2003 | Dutta |
| 6,641,557 B1 | 11/2003 | Frazier et al. |
| 6,651,303 B1 | 11/2003 | Toivanen et al. |
| 6,652,555 B1 | 11/2003 | VanTassel et al. |
| 6,652,556 B1 | 11/2003 | VanTassel et al. |
| 6,666,861 B1 | 12/2003 | Grabek |
| 6,689,150 B1 | 2/2004 | VanTassel et al. |
| 6,712,804 B2 | 3/2004 | Roue et al. |
| 6,712,810 B2 | 3/2004 | Harrington et al. |
| 6,723,108 B1 | 4/2004 | Jones et al. |
| 6,730,108 B2 | 5/2004 | Van Tassel et al. |
| 6,881,875 B2 | 4/2005 | Swenson |
| 6,941,169 B2 | 9/2005 | Pappu |
| 6,949,113 B2 | 9/2005 | Van Tassel et al. |
| 6,977,323 B1 | 12/2005 | Swenson |
| 6,979,344 B2 | 12/2005 | Jones et al. |
| 6,994,092 B2 | 2/2006 | Van Der et al. |
| 7,011,671 B2 | 3/2006 | Welch |
| 7,044,134 B2 | 5/2006 | Khairkhahan et al. |
| 7,056,294 B2 | 6/2006 | Khairkhahan et al. |
| 7,115,110 B2 | 10/2006 | Frazier et al. |
| 7,128,073 B1 | 10/2006 | Van der Burg et al. |
| 7,152,605 B2 | 12/2006 | Khairkhahan et al. |
| 7,169,164 B2 | 1/2007 | Borillo et al. |
| 7,192,439 B2 | 3/2007 | Khairkhahan et al. |
| 7,226,458 B2 | 6/2007 | Kaplan et al. |
| 7,291,382 B2 | 11/2007 | Krueger et al. |
| 7,293,562 B2 | 11/2007 | Malecki |
| 7,318,829 B2 | 1/2008 | Kaplan et al. |
| 7,344,543 B2 | 3/2008 | Sra |
| 7,358,282 B2 | 4/2008 | Krueger et al. |
| 7,427,279 B2 | 9/2008 | Frazier et al. |
| 7,549,983 B2 | 6/2009 | Roue et al. |
| 7,566,336 B2 | 7/2009 | Corcoran et al. |
| 7,597,704 B2 | 10/2009 | Frazier et al. |
| 7,695,425 B2 | 4/2010 | Schweich et al. |
| 7,713,282 B2 | 5/2010 | Frazier et al. |
| 7,722,641 B2 | 5/2010 | Van Der et al. |
| 7,727,189 B2 | 6/2010 | VanTassel et al. |
| 7,735,493 B2 | 6/2010 | van der Burg et al. |
| 7,747,047 B2 | 6/2010 | Okerlund et al. |
| 7,780,683 B2 | 8/2010 | Roue et al. |
| 7,803,395 B2 | 9/2010 | Datta et al. |
| 7,824,397 B2 | 11/2010 | Mcauley |
| 7,922,716 B2 | 4/2011 | Malecki et al. |
| 7,972,359 B2 | 7/2011 | Kreidler |
| 7,998,138 B2 | 8/2011 | Mcauley |
| 8,043,329 B2 | 10/2011 | Khairkhahan et al. |
| 8,052,715 B2 | 11/2011 | Quinn et al. |
| 8,057,530 B2 | 11/2011 | Kusleika et al. |
| 8,080,032 B2 | 12/2011 | van der Burg et al. |
| 8,097,015 B2 | 1/2012 | Devellian |
| 8,142,470 B2 | 3/2012 | Quinn et al. |
| 8,157,818 B2 | 4/2012 | Gartner et al. |
| 8,197,496 B2 | 6/2012 | Roue et al. |
| 8,197,527 B2 | 6/2012 | Borillo et al. |
| 8,221,445 B2 | 7/2012 | Van Tassel et al. |
| 8,262,694 B2 | 9/2012 | Widomski et al. |
| 8,287,563 B2 | 10/2012 | Khairkhahan et al. |
| 8,313,504 B2 | 11/2012 | Do et al. |
| 8,323,309 B2 | 12/2012 | Khairkhahan et al. |
| 8,337,487 B2 | 12/2012 | Datta et al. |
| 8,361,111 B2 | 1/2013 | Widomski et al. |
| 8,460,282 B2 | 6/2013 | Mcauley |
| 8,480,708 B2 | 7/2013 | Kassab et al. |
| 8,523,897 B2 | 9/2013 | Van Der et al. |
| 8,535,343 B2 | 9/2013 | Van Der et al. |
| 8,540,760 B2 | 9/2013 | Paul, Jr. et al. |
| 8,603,108 B2 | 12/2013 | Roue et al. |
| 8,636,764 B2 | 1/2014 | Miles et al. |
| 8,690,911 B2 | 1/2014 | Miles et al. |
| 8,647,361 B2 | 2/2014 | Borillo et al. |
| 8,647,367 B2 | 2/2014 | Kassab et al. |
| 8,663,268 B2 | 3/2014 | Quinn et al. |
| 8,663,273 B2 | 3/2014 | Khairkhahan et al. |
| 8,685,055 B2 | 4/2014 | VanTassel et al. |
| 8,715,302 B2 | 5/2014 | Ibrahim et al. |
| 8,715,318 B2 | 5/2014 | Miles |
| 8,740,934 B2 | 7/2014 | McGuckin, Jr. |
| 8,764,793 B2 * | 7/2014 | Lee .................. A61B 17/0057 606/213 |
| 8,784,469 B2 | 7/2014 | Kassab |
| 8,795,328 B2 | 8/2014 | Miles et al. |
| 8,801,746 B1 | 8/2014 | Kreidler et al. |
| 8,828,051 B2 | 9/2014 | Javois et al. |
| 8,834,519 B2 | 9/2014 | van der Burg et al. |
| 8,840,641 B2 | 9/2014 | Miles et al. |
| 8,845,711 B2 | 9/2014 | Miles et al. |
| 9,011,551 B2 | 4/2015 | Oral et al. |
| 9,034,006 B2 | 5/2015 | Quinn et al. |
| 9,089,313 B2 | 7/2015 | Roue et al. |
| 9,131,849 B2 | 9/2015 | Khairkhahan et al. |
| 9,132,000 B2 | 9/2015 | VanTassel et al. |

(56) References Cited

U.S. PATENT DOCUMENTS

| | | |
|---|---|---|
| 9,161,830 B2 | 10/2015 | Borillo et al. |
| 9,168,043 B2 | 10/2015 | Van Der et al. |
| 9,186,152 B2 | 11/2015 | Campbell et al. |
| 9,351,716 B2 | 5/2016 | Miles et al. |
| 9,421,004 B2 | 8/2016 | Roue et al. |
| 9,445,895 B2 | 9/2016 | Kreidler |
| 9,474,516 B2 | 10/2016 | Clark et al. |
| 9,554,804 B2 | 1/2017 | Erzberger et al. |
| 9,592,058 B2 | 3/2017 | Erzberger et al. |
| 9,592,110 B1 | 3/2017 | Dan et al. |
| 9,649,115 B2 | 5/2017 | Edmiston et al. |
| 9,693,780 B2 | 7/2017 | Miles et al. |
| 9,693,781 B2 | 7/2017 | Miles et al. |
| 9,700,323 B2 | 7/2017 | Clark |
| 9,730,701 B2 | 8/2017 | Tischler et al. |
| 9,743,932 B2 | 8/2017 | Amplatz et al. |
| 9,763,666 B2 | 9/2017 | Wu et al. |
| 9,808,253 B2 | 11/2017 | Li et al. |
| 9,839,431 B2 | 12/2017 | Meyer et al. |
| 9,849,011 B2 | 12/2017 | Zimmerman et al. |
| 9,861,370 B2 | 1/2018 | Clark et al. |
| 9,883,864 B2 | 2/2018 | Miles et al. |
| 9,883,936 B2 | 2/2018 | Sutton et al. |
| 9,913,652 B2 | 3/2018 | Bridgeman et al. |
| 9,943,299 B2 | 4/2018 | Khairkhahan et al. |
| 9,943,315 B2 | 4/2018 | Kaplan et al. |
| 10,617,425 B2 | 4/2020 | Kaplan et al. |
| 10,722,240 B1 | 7/2020 | Melanson et al. |
| 11,026,695 B2 | 6/2021 | Melanson et al. |
| 11,109,868 B2 | 9/2021 | Forbes |
| 11,116,510 B2 | 9/2021 | Melanson |
| 11,123,079 B2 | 9/2021 | Andserson |
| 11,123,080 B2 | 9/2021 | Lashinski |
| 11,134,934 B2 | 10/2021 | Rafiee |
| 11,154,303 B2 | 10/2021 | Miles |
| 11,166,703 B2 | 11/2021 | Kassab |
| 11,191,546 B2 | 12/2021 | Gong |
| 11,191,547 B2 | 12/2021 | Deville |
| 11,207,073 B2 | 12/2021 | Clark |
| 11,213,282 B2 | 1/2022 | Maslanka |
| 11,219,462 B2 | 1/2022 | Lashinski |
| 11,224,435 B2 | 1/2022 | Fung |
| 11,241,237 B2 | 2/2022 | Tischler |
| 11,241,239 B2 | 2/2022 | Cao |
| 11,253,241 B2 | 2/2022 | Li |
| 11,253,262 B2 | 2/2022 | Miles |
| 11,266,389 B2 | 3/2022 | Sternik |
| 11,284,871 B2 | 3/2022 | Corcoran |
| 11,284,899 B2 | 3/2022 | Ibrahim |
| 11,291,454 B2 | 4/2022 | Chen |
| 11,317,920 B2 | 5/2022 | Amplatz |
| 11,324,510 B2 | 5/2022 | Morejohn |
| 11,331,104 B2 | 5/2022 | Inouye |
| 11,337,684 B2 | 5/2022 | Zhang |
| 11,344,312 B2 | 5/2022 | Wang |
| 11,344,313 B2 | 5/2022 | Otero |
| 11,344,733 B2 | 5/2022 | Kaiser |
| 11,350,944 B2 | 6/2022 | Liddicoat |
| 11,357,512 B2 | 6/2022 | Fishel |
| 11,369,355 B2 | 6/2022 | Lee |
| 11,369,374 B2 | 6/2022 | Wheeler |
| 11,369,780 B2 | 6/2022 | Rabito |
| 11,389,167 B2 | 7/2022 | Clark |
| 11,399,842 B2 | 8/2022 | Kaplan |
| 11,399,843 B2 | 8/2022 | Lashinski |
| 11,413,047 B2 | 8/2022 | Clark |
| 11,413,048 B2 | 8/2022 | Anderson |
| 11,419,591 B2 | 8/2022 | Liu |
| 11,419,611 B2 | 8/2022 | Sharma |
| 11,426,172 B2 | 8/2022 | Melanson |
| 11,432,809 B2 | 9/2022 | Inouye et al. |
| 11,432,875 B2 | 9/2022 | Camus |
| 11,484,320 B2 | 11/2022 | Kangas |
| 11,484,397 B2 | 11/2022 | Dan et al. |
| 11,497,505 B2 | 11/2022 | Slaughter et al. |
| 11,497,636 B2 | 11/2022 | Xiao et al. |
| 11,512,416 B2 | 11/2022 | Koppe |
| 11,534,174 B2 | 12/2022 | Amplatz et al. |
| 11,534,175 B2 | 12/2022 | Hill |
| 11,534,320 B2 | 12/2022 | Westhoff et al. |
| 11,540,836 B2 | 1/2023 | Wang et al. |
| 11,540,837 B2 | 1/2023 | Edminston et al. |
| 11,540,838 B2 | 1/2023 | Groff et al. |
| 11,547,416 B2 | 1/2023 | Berger et al. |
| 11,547,417 B2 | 1/2023 | Li et al. |
| 2002/0022860 A1* | 2/2002 | Borillo ............ A61B 17/12022 606/200 |
| 2002/0049457 A1 | 4/2002 | Kaplan et al. |
| 2002/0095205 A1 | 7/2002 | Edwin et al. |
| 2002/0099390 A1 | 7/2002 | Kaplan et al. |
| 2002/0103492 A1 | 8/2002 | Kaplan et al. |
| 2002/0111637 A1 | 8/2002 | Kaplan et al. |
| 2002/0111647 A1 | 8/2002 | Khairkhahan et al. |
| 2002/0169377 A1 | 11/2002 | Khairkhahan et al. |
| 2003/0023266 A1 | 1/2003 | Borillo et al. |
| 2003/0051735 A1* | 3/2003 | Pavcnik ............ A61B 17/0057 128/831 |
| 2003/0120337 A1 | 6/2003 | Van Tassel et al. |
| 2003/0191526 A1 | 10/2003 | Van Tassel et al. |
| 2003/0199923 A1 | 10/2003 | Khairkhahan et al. |
| 2003/0204203 A1 | 10/2003 | Khairkhahan et al. |
| 2003/0220667 A1 | 11/2003 | van der Burg et al. |
| 2004/0044361 A1 | 3/2004 | Frazier et al. |
| 2004/0049210 A1 | 3/2004 | VanTassel et al. |
| 2004/0098031 A1 | 5/2004 | van der Burg et al. |
| 2004/0122467 A1 | 6/2004 | VanTassel et al. |
| 2004/0127935 A1 | 7/2004 | VanTassel et al. |
| 2004/0215230 A1 | 10/2004 | Frazier et al. |
| 2004/0220610 A1 | 11/2004 | Kreidler et al. |
| 2004/0225212 A1 | 11/2004 | Okerlund et al. |
| 2004/0230222 A1 | 11/2004 | van der Burg et al. |
| 2005/0004652 A1 | 1/2005 | van der Burg et al. |
| 2005/0033287 A1 | 2/2005 | Sra |
| 2005/0038470 A1 | 2/2005 | van der Burg et al. |
| 2005/0049573 A1 | 3/2005 | VanTassel et al. |
| 2005/0070952 A1 | 3/2005 | Devellian |
| 2005/0113861 A1 | 5/2005 | Corcoran et al. |
| 2005/0149068 A1 | 7/2005 | Williams et al. |
| 2005/0149069 A1 | 7/2005 | Bertolero et al. |
| 2005/0177182 A1 | 8/2005 | van der Burg et al. |
| 2005/0203568 A1* | 9/2005 | Burg .................... A61M 25/10 606/200 |
| 2005/0234540 A1 | 10/2005 | Peavey et al. |
| 2005/0234543 A1 | 10/2005 | Glaser et al. |
| 2005/0267528 A1* | 12/2005 | Ginn ................ A61B 17/0057 606/214 |
| 2006/0009715 A1 | 1/2006 | Khairkhahan et al. |
| 2006/0116709 A1* | 6/2006 | Sepetka ........... A61B 17/12022 606/200 |
| 2007/0005147 A1 | 1/2007 | Levine |
| 2007/0083230 A1 | 4/2007 | Javois |
| 2007/0129753 A1 | 6/2007 | Quinn et al. |
| 2007/0135826 A1 | 6/2007 | Zaver et al. |
| 2007/0149988 A1 | 6/2007 | Michler et al. |
| 2007/0149995 A1 | 6/2007 | Quinn et al. |
| 2007/0179345 A1 | 8/2007 | Santilli |
| 2007/0270891 A1 | 11/2007 | McGuckin, Jr. |
| 2007/0293934 A1 | 12/2007 | Grewe |
| 2008/0033241 A1 | 2/2008 | Peh et al. |
| 2008/0125795 A1 | 5/2008 | Kaplan et al. |
| 2008/0243183 A1 | 10/2008 | Miller et al. |
| 2008/0294175 A1 | 11/2008 | Bardsley et al. |
| 2008/0312664 A1 | 12/2008 | Bardsley et al. |
| 2009/0005760 A1 | 1/2009 | Cartledge |
| 2009/0099596 A1 | 4/2009 | McGunkin, Jr. et al. |
| 2009/0112249 A1* | 4/2009 | Miles ................ A61B 17/1214 606/192 |
| 2009/0143791 A1 | 6/2009 | Miller et al. |
| 2009/0157118 A1 | 6/2009 | Miller et al. |
| 2009/0264920 A1 | 10/2009 | Berenstein |
| 2009/0287145 A1 | 11/2009 | Cragg et al. |
| 2009/0306685 A1 | 12/2009 | Fill |
| 2009/0326577 A1 | 12/2009 | Johnson et al. |
| 2010/0076463 A1 | 3/2010 | Mavani et al. |

(56) References Cited

U.S. PATENT DOCUMENTS

| | | |
|---|---|---|
| 2010/0191279 A1 | 7/2010 | Kassab et al. |
| 2010/0228184 A1 | 9/2010 | Mavani et al. |
| 2010/0228279 A1 | 9/2010 | Miles et al. |
| 2010/0228285 A1 | 9/2010 | Miles et al. |
| 2010/0286718 A1 | 11/2010 | Kassab et al. |
| 2010/0324585 A1 | 12/2010 | Miles et al. |
| 2010/0324586 A1 | 12/2010 | Miles et al. |
| 2010/0324587 A1 | 12/2010 | Miles et al. |
| 2010/0324588 A1 | 12/2010 | Miles et al. |
| 2011/0009853 A1 | 1/2011 | Bertolero et al. |
| 2011/0022079 A1 | 1/2011 | Miles et al. |
| 2011/0022168 A1 | 1/2011 | Cartledge |
| 2011/0054515 A1 | 3/2011 | Bridgeman et al. |
| 2011/0082495 A1 | 4/2011 | Ruiz |
| 2011/0087271 A1 | 4/2011 | Sargeant et al. |
| 2011/0178539 A1 | 7/2011 | Holmes, Jr. et al. |
| 2011/0208233 A1 | 8/2011 | McGunkin, Jr. et al. |
| 2011/0218389 A1 | 9/2011 | Gobel |
| 2011/0218566 A1 | 9/2011 | van der Burg et al. |
| 2011/0220120 A1 | 9/2011 | Frigstad et al. |
| 2011/0257674 A1 | 10/2011 | Evert et al. |
| 2011/0264119 A1 | 10/2011 | Bayon et al. |
| 2011/0307003 A1 | 12/2011 | Chambers |
| 2011/0313507 A1 | 12/2011 | Miranda et al. |
| 2012/0010644 A1 | 1/2012 | Sideris et al. |
| 2012/0029553 A1 | 2/2012 | Quinn et al. |
| 2012/0065662 A1 | 3/2012 | van der Burg et al. |
| 2012/0065667 A1 | 3/2012 | Javois et al. |
| 2012/0157916 A1 | 6/2012 | Quinn et al. |
| 2012/0158022 A1 | 6/2012 | Kaplan et al. |
| 2012/0172927 A1 | 7/2012 | Campbell et al. |
| 2012/0221042 A1 | 8/2012 | Schwartz et al. |
| 2012/0239077 A1 | 9/2012 | Zaver et al. |
| 2012/0283585 A1 | 11/2012 | Werneth et al. |
| 2012/0283773 A1 | 11/2012 | VanTassel et al. |
| 2012/0316584 A1 | 12/2012 | Miles et al. |
| 2012/0323262 A1 | 12/2012 | Ibrahim et al. |
| 2012/0323267 A1 | 12/2012 | Ren |
| 2012/0323270 A1 | 12/2012 | Lee |
| 2012/0330342 A1* | 12/2012 | Jones ............... A61F 2/01 606/194 |
| 2013/0006343 A1 | 1/2013 | Kassab |
| 2013/0012982 A1 | 1/2013 | Khairkhahan et al. |
| 2013/0018413 A1 | 1/2013 | Oral et al. |
| 2013/0018414 A1 | 1/2013 | Widomski et al. |
| 2013/0083983 A1 | 4/2013 | Zhong et al. |
| 2013/0110154 A1 | 5/2013 | van der Burg et al. |
| 2013/0116724 A1 | 5/2013 | Clark et al. |
| 2013/0165965 A1 | 6/2013 | Carlson et al. |
| 2013/0178889 A1 | 7/2013 | Miles |
| 2013/0237908 A1 | 9/2013 | Clark |
| 2014/0005714 A1 | 1/2014 | Quick et al. |
| 2014/0046360 A1 | 2/2014 | van der Burg et al. |
| 2014/0074151 A1 | 3/2014 | Tischler et al. |
| 2014/0128903 A1 | 5/2014 | Alferness |
| 2014/0135817 A1 | 5/2014 | Tischler et al. |
| 2014/0257320 A1 | 9/2014 | Fitz |
| 2014/0277074 A1 | 9/2014 | Kaplan et al. |
| 2014/0330368 A1 | 11/2014 | Gloss |
| 2014/0336699 A1 | 11/2014 | van der Burg et al. |
| 2014/0364941 A1 | 12/2014 | Edmiston et al. |
| 2014/0371789 A1 | 12/2014 | Hariton et al. |
| 2015/0005810 A1 | 1/2015 | Center et al. |
| 2015/0039021 A1 | 2/2015 | Khairkhahan et al. |
| 2015/0133989 A1 | 5/2015 | Lubeck et al. |
| 2015/0196305 A1 | 7/2015 | Meyer et al. |
| 2016/0058539 A1 | 1/2016 | Vantassel et al. |
| 2016/0089151 A1 | 3/2016 | Siegel et al. |
| 2016/0106437 A1 | 4/2016 | van der Burg et al. |
| 2016/0278784 A1 | 9/2016 | Edmiston |
| 2017/0042549 A1 | 2/2017 | Kaplan et al. |
| 2017/0042550 A1 | 2/2017 | Chakraborty et al. |
| 2017/0095238 A1 | 4/2017 | Rudman et al. |
| 2017/0100112 A1 | 4/2017 | Van Der et al. |
| 2017/0135801 A1 | 5/2017 | Delaney, Jr. et al. |
| 2017/0224354 A1 | 8/2017 | Tischler et al. |
| 2017/0281192 A1 | 10/2017 | Tieu et al. |
| 2017/0290594 A1 | 10/2017 | Chakraborty et al. |
| 2017/0340336 A1 | 11/2017 | Osypka |
| 2018/0116678 A1 | 5/2018 | Melanson |
| 2018/0185130 A1 | 7/2018 | Janardhan et al. |
| 2018/0206830 A1 | 7/2018 | Khairkhahan et al. |
| 2018/0250014 A1 | 9/2018 | Melanson et al. |
| 2018/0338824 A1 | 11/2018 | VanTassel et al. |
| 2019/0083075 A1 | 3/2019 | Onushko et al. |
| 2019/0125362 A1 | 5/2019 | Tischler |
| 2019/0336137 A1 | 11/2019 | Chakraborty et al. |
| 2020/0253614 A1 | 8/2020 | Melanson |
| 2020/0269059 A1 | 8/2020 | Kaiser |
| 2021/0169500 A1 | 6/2021 | Melanson et al. |
| 2021/0275183 A1 | 9/2021 | Amplatz |
| 2021/0282757 A1 | 9/2021 | Manash et al. |
| 2021/0298728 A1 | 9/2021 | Lashinski |
| 2021/0298763 A1 | 9/2021 | Stahmann |
| 2021/0298764 A1 | 9/2021 | Subramaniam |
| 2021/0330333 A1 | 10/2021 | Gray |
| 2021/0346033 A1 | 11/2021 | Horton |
| 2021/0346706 A1 | 11/2021 | Devich |
| 2021/0353354 A1 | 11/2021 | Schuler |
| 2021/0369283 A1 | 12/2021 | O'Halloran |
| 2021/0369284 A1 | 12/2021 | Lashinski |
| 2021/0378679 A1 | 12/2021 | Amplatz |
| 2021/0393271 A1 | 12/2021 | Melanson |
| 2021/0401418 A1 | 12/2021 | Dang |
| 2022/0000488 A1 | 1/2022 | Anderson |
| 2022/0022854 A1 | 1/2022 | Lashinski |
| 2022/0022880 A1 | 1/2022 | Dosta |
| 2022/0031333 A1 | 2/2022 | Zhou |
| 2022/0054117 A1 | 2/2022 | Rafiee |
| 2022/0061829 A1 | 3/2022 | Kassab |
| 2022/0079600 A1 | 3/2022 | Moriyama |
| 2022/0079667 A1 | 3/2022 | Gabay |
| 2022/0087664 A1 | 3/2022 | Maslanka |
| 2022/0087683 A1 | 3/2022 | Fishel |
| 2022/0087684 A1 | 3/2022 | Edminston |
| 2022/0087741 A1 | 3/2022 | Lashinski |
| 2022/0088355 A1 | 3/2022 | Rabito |
| 2022/0096093 A1 | 3/2022 | Centola |
| 2022/0104830 A1 | 4/2022 | Centola |
| 2022/0117555 A1 | 4/2022 | Zarbatany |
| 2022/0117608 A1 | 4/2022 | Tischler |
| 2022/0117764 A1 | 4/2022 | Jiang |
| 2022/0133178 A1 | 5/2022 | Li |
| 2022/0133261 A1 | 5/2022 | Urman |
| 2022/0167989 A1 | 6/2022 | Ibrahim |
| 2022/0175390 A1 | 6/2022 | Lee |
| 2022/0175391 A1 | 6/2022 | Zhou |
| 2022/0192676 A9 | 6/2022 | Kaplan |
| 2022/0202401 A1 | 6/2022 | Isilki |
| 2022/0211386 A1 | 7/2022 | Amplatz |
| 2022/0218355 A1 | 7/2022 | Wedul |
| 2022/0240941 A1 | 8/2022 | Lashinski |
| 2022/0249101 A1 | 8/2022 | Min |
| 2022/0257259 A1 | 8/2022 | Li |
| 2022/0257955 A1 | 8/2022 | Zarbatany |
| 2022/0265280 A1 | 8/2022 | Chamorro |
| 2022/0280144 A1 | 9/2022 | Lee |
| 2022/0287697 A1 | 9/2022 | Roche |
| 2022/0287713 A1 | 9/2022 | Wheeler |
| 2022/0287720 A1 | 9/2022 | Otero |
| 2022/0296306 A1 | 9/2022 | Camus |
| 2022/0313270 A1 | 10/2022 | Inouye et al. |
| 2022/0330948 A1 | 10/2022 | Lee et al. |
| 2022/0331104 A1 | 10/2022 | Rafiee |
| 2022/0338877 A1 | 10/2022 | Natesan et al. |
| 2022/0346796 A1 | 11/2022 | Morejohn et al. |
| 2022/0354472 A1 | 11/2022 | Berger et al. |
| 2022/0354501 A1 | 11/2022 | Clark et al. |
| 2022/0361864 A1 | 11/2022 | Liu et al. |
| 2022/0370079 A1 | 11/2022 | Harari et al. |
| 2022/0387043 A1 | 12/2022 | Centola |
| 2022/0387757 A1 | 12/2022 | Wang et al. |
| 2022/0395279 A1 | 12/2022 | Chen et al. |
| 2022/0401109 A1 | 12/2022 | Zarbatany et al. |

(56) References Cited

U.S. PATENT DOCUMENTS

| | | |
|---|---|---|
| 2022/0401110 A1 | 12/2022 | Dinges et al. |
| 2022/0401112 A1 | 12/2022 | Zhou et al. |
| 2022/0409211 A1 | 12/2022 | Moszner |
| 2022/0409255 A1 | 12/2022 | Li et al. |
| 2023/0008857 A1 | 1/2023 | Tu et al. |
| 2023/0010024 A1 | 1/2023 | Chen et al. |
| 2023/0012824 A1 | 1/2023 | O'Halloran et al. |
| 2023/0018512 A1 | 1/2023 | O'Halloran et al. |
| 2023/0032647 A1 | 2/2023 | Kaplan et al. |
| 2023/0071677 A1 | 3/2023 | Melanson et al. |

FOREIGN PATENT DOCUMENTS

| | | |
|---|---|---|
| DE | 102006056283 A1 | 6/2008 |
| EP | 1223890 B1 | 4/2004 |
| EP | 1227770 B1 | 9/2004 |
| EP | 1225843 B1 | 2/2005 |
| EP | 1469790 B1 | 10/2016 |
| EP | 3085310 A1 | 10/2016 |
| EP | 2872051 B1 | 3/2017 |
| EP | 3531926 A2 | 9/2019 |
| JP | 2003-512128 | 4/2003 |
| JP | 2003-529384 | 10/2003 |
| JP | 2012-515624 | 11/2012 |
| JP | 2012-530551 | 12/2012 |
| JP | 2014-531247 | 11/2014 |
| JP | 2014-534872 | 12/2014 |
| JP | 2015-534881 | 12/2015 |
| JP | 2016-518155 | 6/2016 |
| JP | 2016-202905 | 12/2016 |
| WO | WO 00/27292 | 5/2000 |
| WO | WO2009009466 | 1/2009 |
| WO | WO 2010/148246 | 12/2010 |
| WO | WO 2013/067188 | 5/2013 |
| WO | WO2014/011865 | 1/2014 |
| WO | WO 2014/078531 | 5/2014 |
| WO | WO 2014/178531 | 5/2014 |
| WO | WO 2014/164572 | 10/2014 |
| WO | WO2016/033170 | 3/2016 |
| WO | WO 2017/066197 | 4/2017 |
| WO | WO 2017/161283 | 9/2017 |
| WO | WO 2018/081466 | 5/2018 |
| WO | WO2018/185255 | 10/2018 |
| WO | WO2018/185256 | 10/2018 |
| WO | WO 2019/033121 | 2/2019 |
| WO | WO 2019/212894 | 11/2019 |
| WO | WO 2020/163507 | 8/2020 |
| WO | WO 2020/185389 | 9/2020 |
| WO | WO 2022/182565 | 9/2022 |

OTHER PUBLICATIONS

Möbius-Winkler, S., Sandri, M., Mangner, N., Lurz, P., Dähnert, I., Schuler, G. "The Watchman Left Atrial Appendage Closure Device for Atrial Fibrillation," J. Vis. Exp. (60), e3671, DOI : 10.3791/3671 (Feb. 28, 2012).

International Search Report and Written Opinion dated Jul. 3, 2014, in International Application No. PCT/US2014/022865.

Extended European Search Report in European Patent Case No. EP 14 77 9640 dated Sep. 30, 2016.

International Search Report and Written Opinion dated Jan. 19, 2017, in International Application No. PCT/US2016/056450.

International Search Report and Written Opinion dated Jun. 8, 2020, in International Application No. PCT/US2020/016854.

International Search Report and Written Opinion from PCT Application PCT/US2017/058600 dated Jun. 13, 2018.

International Search Report and Written Opinion from PCT Application PCT/US2022/016766 dated Jul. 5, 2022.

\* cited by examiner

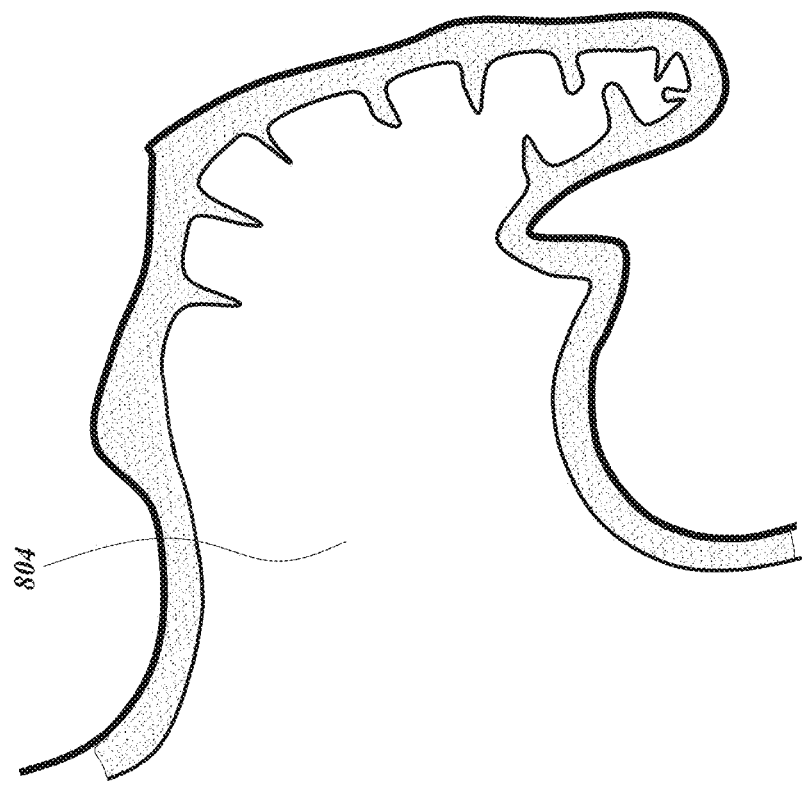
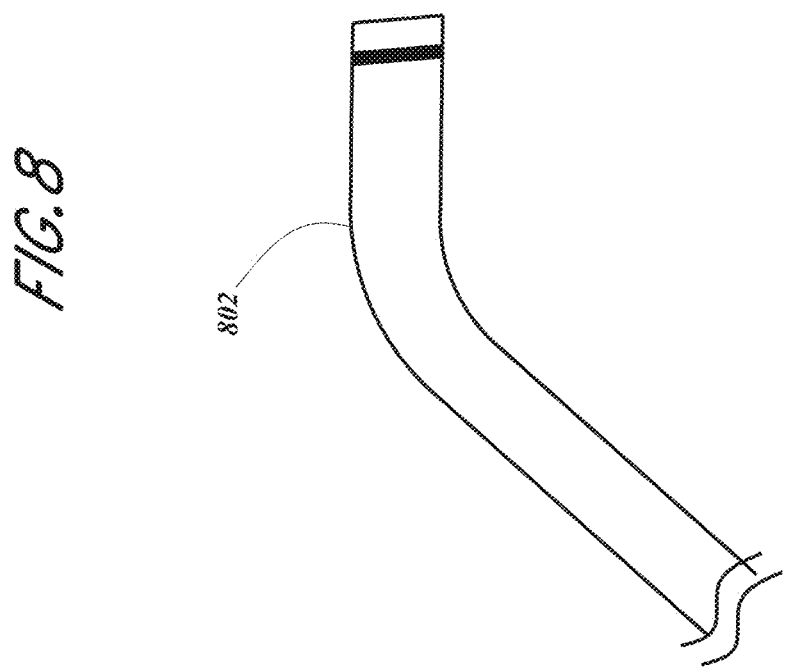
FIG. 8

DEVICES AND METHODS FOR EXCLUDING THE LEFT ATRIAL APPENDAGE

CROSS-REFERENCE TO RELATED APPLICATIONS

Any and all applications for which a foreign or domestic priority claim is identified in the Application Data Sheet as filed with the present application are hereby incorporated by reference under 37 CFR 1.57. For example, this application is a continuation application of U.S. patent application Ser. No. 14/203,187, filed Mar. 10, 2014, which claims the priority benefit under 35 U.S.C. § 119(e) of U.S. Provisional Application No. 61/779,802, filed Mar. 13, 2013, the entirety of each of which is hereby incorporated by reference herein.

FIELD OF THE INVENTION

The embodiments disclosed herein relate to devices and methods for occluding the left atrial appendage (LAA) to prevent blood from clotting within the LAA and subsequently embolizing, particularly in patients with atrial fibrillation.

BACKGROUND OF THE INVENTION

Atrial fibrillation (Afib) is a condition in which the normal beating of the left atrium (LA) is chaotic and ineffective. The left atrial appendage (LAA) is a blind pouch off the LA. In patients with Afib blood stagnates in the LAA facilitating clot formation. These clots (or clot fragments) have a tendency to embolize or leave the LAA and enter the systemic circulation. A stroke occurs when clot/clot fragment embolizes and occludes one of the arteries perfusing the brain. Anticoagulants, e.g. Coumadin, have been shown to significantly reduce the stroke risk in Afib patients. These drugs reduce clot formation but also increased bleeding complications including hemorrhagic strokes, subdural hematoma and bleeding in the gastrointestinal tract.

There are about 8 million people in the US and EU with Afib. About 4.6 million of these patients are at a high risk for stroke and would benefit from anticoagulation. A large portion of these patients cannot take anticoagulants due to an increased bleeding risk leaving their stroke risk unaddressed. The prevalence of Afib increases with age.

Several devices for occluding the LAA are described in the prior art and each has limitations this invention improves upon. The prior art devices are metal structures which are circular in cross section and are made to expand to fill the LAA ostium. These devices are offered in many sizes and must be closely matched to the highly variable LAA anatomy. This is difficult to do using fluoroscopy and often requires adjunctive imaging in the form of transesophageal echocardiography, cardiac CT and MRI, all with three dimensional reconstructions. If the device is significantly oversized, the LAA ostium may become overstretched leading to tearing resulting in bleeding into the pericardial space. If the device is too small, it will not adequately seal the ostium and may be prone to embolization. Even if sized correctly, the device forces the oval LAA ostium to take the round shape of the device, often resulting in residual leakage at the edges due to poor sealing.

Anchoring of these implants in the proper location is described in the prior art devices predominately using an array of radially disposed barbs or hooks which engage into the surrounding cardiac tissue upon expansion of the device. The device must therefore have sufficient spring force or stiffness for the barbs to engage the surrounding tissue. These barbs may lead to leaking of blood through the tissue into the pericardial space which may lead to cardiac tamponade. Furthermore, the geometry of these barbs and hooks prevent additional positioning once the implant is fully expanded.

For all of these reasons it would be desirable to have a device which did not require an excessive number of sizes requiring extensive pre-procedure imaging, could be repositioned when fully expanded and secured without an array of hooks or barbs.

SUMMARY OF THE INVENTION

Devices and methods for occluding the left atrial appendage (LAA) to prevent blood from clotting within the LAA and subsequently embolizing are disclosed herein. These concepts include the ability to deliver a device through a catheter that is tracked over a guide wire through the vascular system. Foams are described that are collapsed for delivery and then expand in place in the LAA. Anchoring of these plugs are made by tissue ingrowth from the LAA into the foams, adhesives, barbs or distal anchoring elements. Foam plugs are described that are encapsulated with jackets that are sufficiently strong to enable handling of the plugs without tearing and also to encourage the creation of a neointima on at least the proximal, LA facing side.

There is provided in accordance with one aspect of the present invention, a left atrial appendage occlusion device. The device comprises an expandable, open cell foam body having a proximal end, a distal end and a side wall. A skin covers at least the proximal (atrial) end of the body, and an expandable lumen extends through the body. The lumen can support a portion of a delivery catheter and/or a guidewire, but collapses to a near zero cross sectional area when such components are removed. This feature reduces the likelihood of emboli forming within the central lumen and dislodging into the bloodstream. The body is compressible within a delivery catheter having an inside diameter of no more than about 20 F and can self expand to a diameter of at least about 25 mm when released from the delivery catheter.

In one implementation of the invention, the skin comprises ePTFE. The skin may extend throughout the length of the guidewire lumen, and may additionally cover at least a portion of the distal end as well as the proximal end of the body. In one embodiment, the skin comprises a tubular ePTFE sleeve, which extends through the guidewire lumen in the open cell foam body, and everts back over the outside of the body, for connection to itself to encase the open cell foam body and line the guidewire lumen.

Preferably, at least one tissue ingrowth surface is provided on the side wall of the body, such as by providing at least one aperture through the skin to place the open cell foam body in direct contact with adjacent tissue. The tissue ingrowth surface may comprise at least about 20%, 40%, 60%, 80% or more of the surface area of the side wall of the body.

At least one radiopaque marker may be provided, such as a radiopaque wire or thread, and/or the foam and/or skin can be loaded with or impregnated with a radiopaque filler such as barium sulfate, bismuth subcarbonate, or tungsten to permit fluoroscopic visualization. At least one or two or more tissue penetrating elements or other anchors may be provided.

In accordance with another aspect of the present invention, there is provided a left atrial appendage closure system. The system comprises a delivery catheter, comprising an elongate flexible tubular body, having a proximal end and a distal end and at least one lumen extending therethrough. A self-expandable open cell foam body compressed within the distal end of the delivery catheter carries a skin covering at least a portion of the body, and a guidewire extending through the body. An axially moveable deployment control such as a push wire extends through the lumen, for deploying the foam body from the distal end of the closure system.

The system may additionally comprise a guidewire, having an inflatable balloon thereon. Preferably, at least one tissue ingrowth area is provided on the body, such as by exposing the open cell foam body through at least one window in the skin.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 8 is a schematic illustration of a guide catheter approaching the ostium to the left atrial appendage.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION OF THE PREFERRED EMBODIMENT

Figure 1:
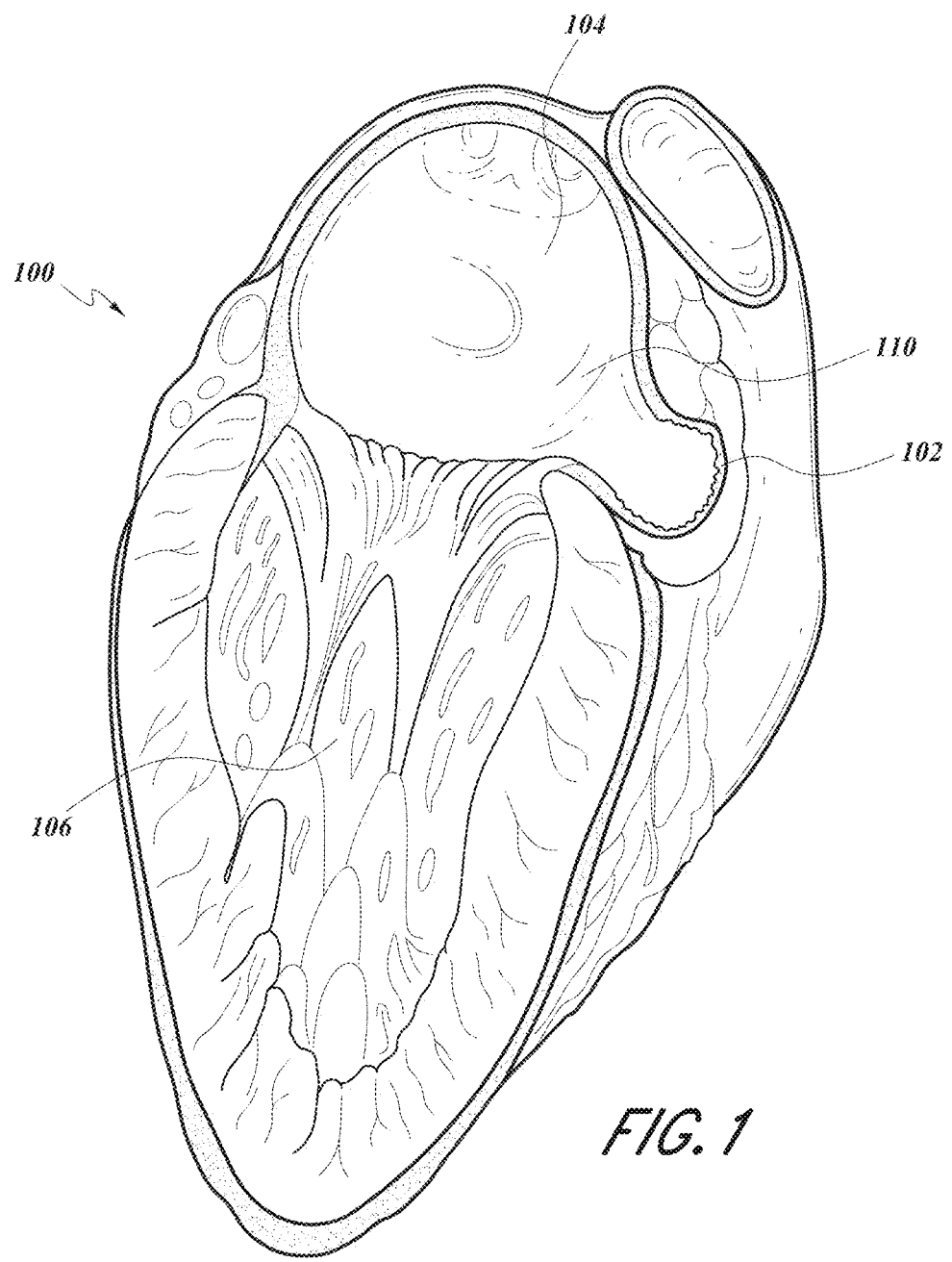
FIG. 1 shows the anatomy of the left atrium and left atrial appendage.

The heart 100 is shown in FIG. 1 with the left atrial appendage (LAA) 102 which is a cavity emanating from the left atrium (LA) 104. The LAA 102 is quite variable in shape in all dimensions. If the heart is not beating normally, a condition called atrial fibrillation, blood within the LAA becomes stagnant which promotes clot formation. If blood clots within the LAA, the clots may pass from the LAA 102 to the LA 104, to the left ventricle 106 and out of the heart 100 into the aorta. Vessels that bring blood to the brain branch off the aorta. If the clot passes to the brain via these vessels, it may get stuck and occlude a small vessel in the brain which then causes an ischemic stroke. Strokes have severe morbidities associated with them.

The opening of the LAA 102 to the LA 104 is called an ostium 110. The object of this invention is to occlude the ostium 110 thereby sealing off the LA 104 from the LAA 102. The ostium 110, is oval, highly variable and dependent of loading conditions, i.e., left atrial pressure.

Figure 2:
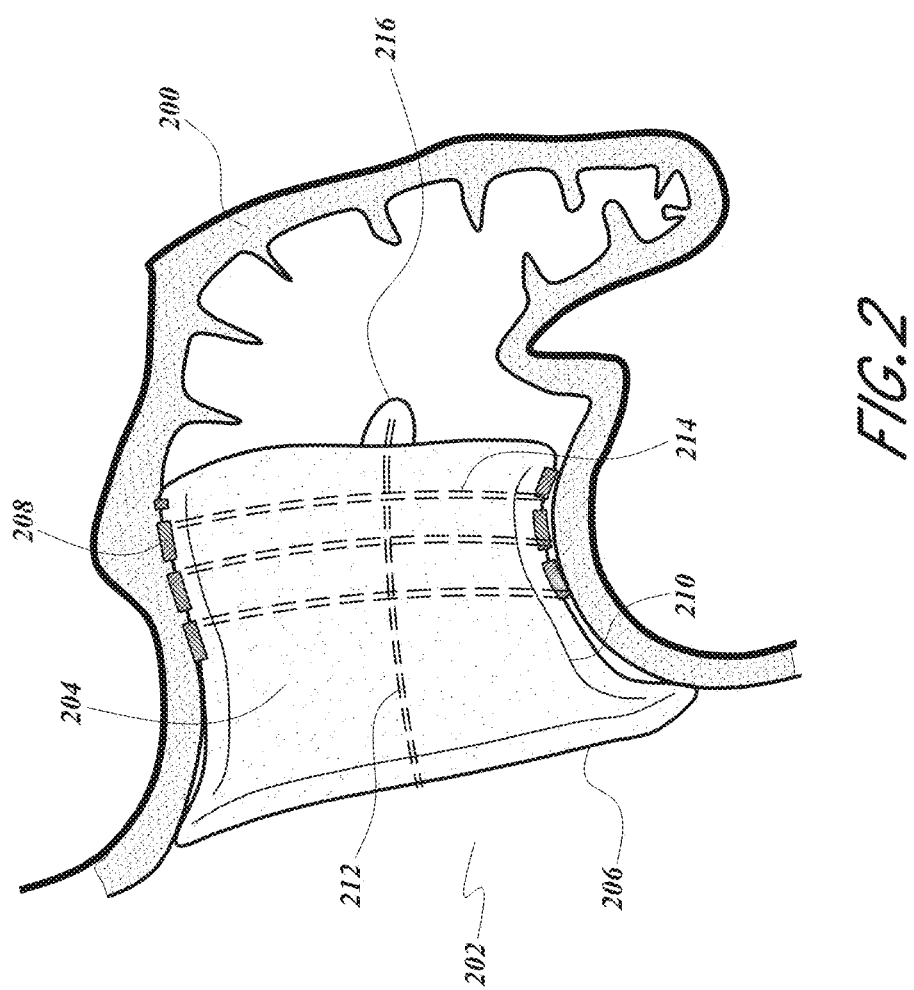
FIG. 2 shows a left atrial appendage with one foam plug embodiment in place that uses adhesive.

One embodiment of the LAA occlusion device is shown in FIG. 2. The occlusion device or plug 204 is placed within the LAA 200 at its opening to the LA 202. The plug 204 comprises an expandable media such as an open cell foam which enables collapse and expansion of the plug and also to enhance ingrowth of tissue into the foam. The foam plug 204 is at least partially encapsulated within a thin strong layer 206 such as ePTFE (expanded polytetrafluoroethylene), polyolefin or polyester. Alternatively bioabsorbable materials could be utilized such as PLA, PGA, PCL, PHA, or collagen. This thin encapsulating layer can be oriented or otherwise modified to be elastomeric in at least one direction, such as radially.

The plug may be made of polyurethane, polyolefin, PVA, collagen foams or blends thereof. One suitable material is a polycarbonate-polyurethane urea foam with a pore size of 100-250 um and 90-95% void content. The foam could be non-degradable or use a degradable material such as PLA, PGA, PCL, PHA, and/or collagen. If degradable, the tissue from the LAA will grow into the foam plug and replace the foam over time. The plug 204 may be cylindrical in shape in an unconstrained expansion but may also be conical with its distal end smaller than the proximal end or reversed. It could also be oval in cross section to better match the opening of the LAA.

The foam plug 204 is oversized radially in an unconstrained expansion to fit snuggly into the LAA and may be 5-50 mm in diameter depending on the diameter of the target LAA. The length of the plug is similar to or greater than its diameter such that the L/D ratio is about or greater than about 1.0 or greater than about 1.5 or greater than about 2.0 to maximize its stability. The compliance of the material is designed such that it pushes on the walls of the LAA with sufficient force to maintain the plug in place but without overly stretching the LAA wall. The foam and/or skin also conforms to the irregular surfaces of the LAA as it expands, to provide a complementary surface structure to the native LAA wall to further enhance anchoring and promote sealing. Thus, while some left atrial appendage occlusion devices in the prior art include a mechanical frame which forces at least some aspect of the left atrial appendage into a circular configuration, the expandable foam implant of the present invention conforms to the native configuration of the left atrial appendage. In one embodiment, the structure of the foam may be fabricated such that squeezing axially on the opposing ends of the foam causes the foam to increase in diameter.

Figure 3:
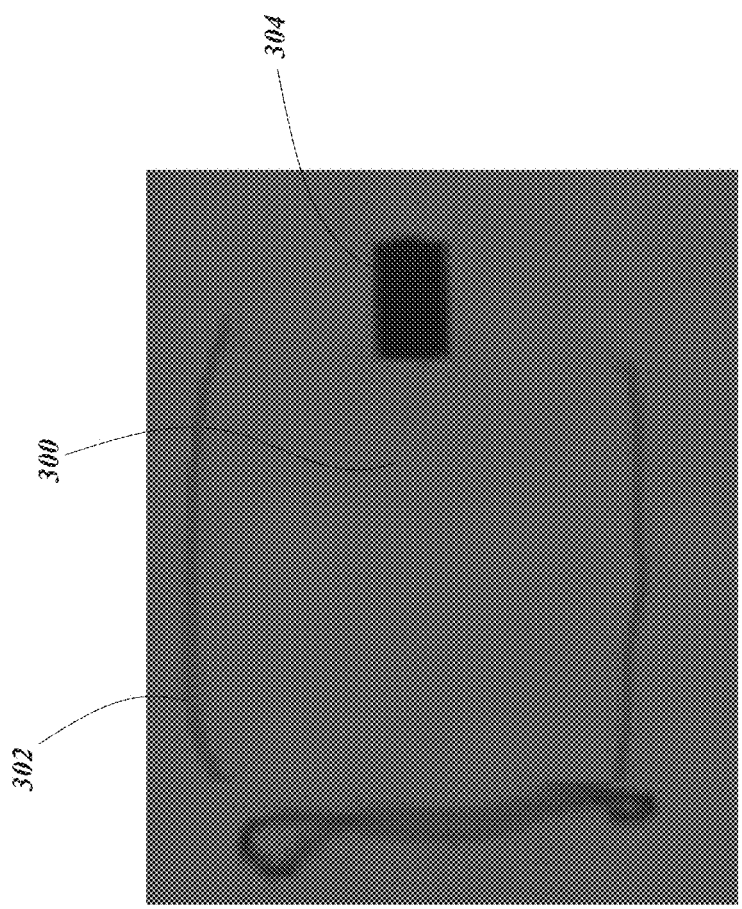
FIG. 3 shows an x-ray image of a foam plug.

The ePTFE or foam material may be provided with one or two or more radiopaque markers such as radiopaque threads 210 or be filled with or impregnated with a radiopaque filler such as barium sulfate, bismuth subcarbonate, or tungsten which permit the operator to see under x-ray the plug for proper positioning in the anatomy. An x-ray image is shown in FIG. 3 where one cannot see the foam plug 300 but can clearly see the threads 302 and the crimp 304 (discussed below). This thread or ribbon may be made from a radiopaque metallic wire such as platinum or tungsten or a polymer with a radiopaque filler such as barium, bismuth, tantalum, tungsten, titanium or platinum.

The outer ePTFE layer may be formed from a tube with a diameter about the same diameter of the foam plug and a wall thickness between about 0.0001" and about 0.001" thick and serves to allow one to collapse and pull on the plug without tearing the foam material. The ePTFE material also serves as the blood contacting surface facing the left atrium 206 and has pores or nodes such that blood components coagulate on the surface and an intimal or neointimal covering of tissue grows across it and anchors tightly to the material. Pore sizes within the range of from about 4μ to about 110μ, ideally 5-35μ are useful for formation and adherence of a neointima.

The outer covering 206 may be constructed of materials other than ePTFE such as woven fabrics, meshes or perforated films made of FEP, polypropylene, polyethylene, polyester or nylon. The covering should have a low compliance (non-elastic), at least longitudinally, be sufficiently strong as to permit removal of the plug, a low coefficient of friction, and be thromboresistant. The outer covering serves as a matrix to permit plug removal as most foams are not sufficiently strong to resist tearing when pulled. The plug can also be coated with or contain materials to enhance its ultrasonic echogenic profile, thromboresistance, lubricity, and/or to facilitate echocardiographic visualization, promote cellular ingrowth and coverage.

The outer covering has holes in it to permit contact of the LAA tissue with the foam plug to encourage ingrowth of tissue into the foam plug pores. These holes may be 1 to 5 mm in diameter or may also be oval with their long axis aligned with the axis of the foam plug, the length of which may be 80% of the length of the foam plug and the width may be 1-5 mm. The holes may be as large as possible such that the outer covering maintains sufficient strength to transmit the tensile forces required for removal. The holes may be preferentially placed along the device. In one embodiment, holes are placed distally to enhance tissue ingrowth from the LAA wall.

Figure 20:
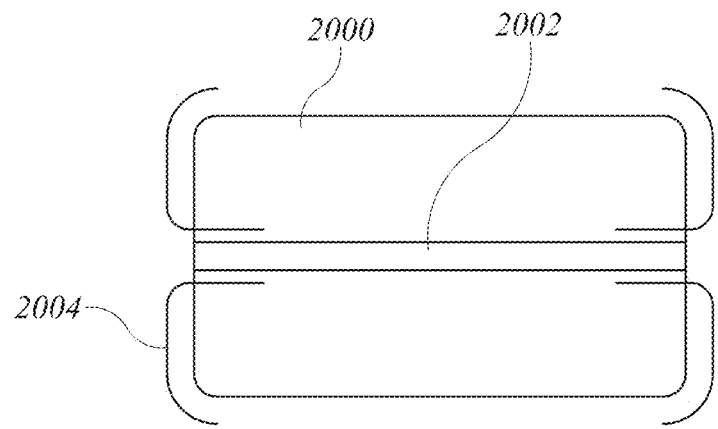
FIG. 20 shows a plug with proximal and distal caps.

In one implementation of the invention, the implant is provided with proximal and distal end caps of ePTFE, joined together by two or three or four or more axially extending strips of ePTFE. The axially extending strips are spaced apart from each other circumferentially, to provide at least two or three or four or more laterally facing windows through which the open cell foam body will be in direct contact with the tissue wall of the left atrial appendage. This outer covering could be a mesh or netting as well. As shown in FIG. 20, the covering 2004 is only on the proximal and distal faces of the plug 2000. They may be glued to the foam plug and then crimped to the center tube 2002.

Figure 21:
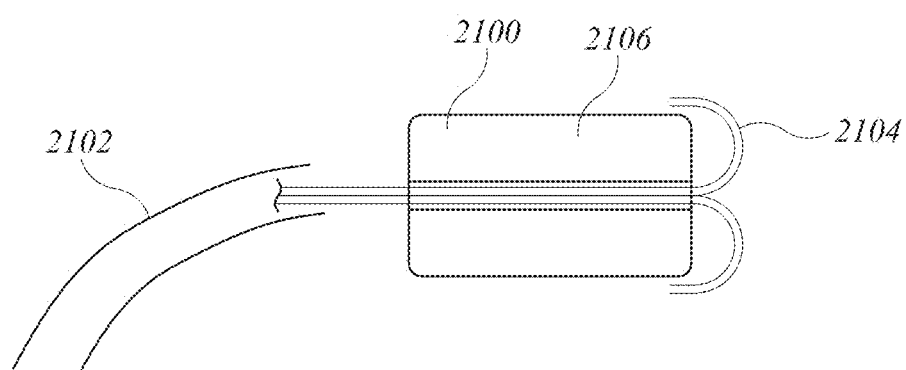
FIG. 21 shows a plug adhesive delivery system.

One means of adhering the foam plug in place within the LAA is to use an adhesive, such as a low viscosity cyanoacrylate (1-200 cps). The adhesive is injected into place along the sidewall near the distal end of the foam plug 208. Holes in the ePTFE covering permit the adhesive to interact between the foam plug 204 and the LAA wall 200. Injection of the adhesive may be accomplished with several means, one of which is to inject through the catheter into the center lumen 212. Passages 214 serve to guide the adhesive to the correct location. The distal end of the foam plug must be restricted at that time to prevent the adhesive from exiting the distal crimp 216. Alternatively, FIG. 21 shows tubes 2104 that are pre-placed through the guide catheter 2102, through the center lumen of the plug 2106 and bend backwards in the LAA to the distal end of the plug 2100. These tubes 2104 pass all the way to the proximal end of the guide catheter 2102 where a fitting is attached to permit injection of the adhesive which then exits the small tubes 2104 at the desired location of the plug. These tubes are made of polyethylene, polypropylene or FEP so that the adhesive will not adhere to the tubes. The tubes 2104 are withdrawn after injection through the guide catheter out of the patient.

Other one part adhesives including aqueous cross linking adhesives, polyurethane, PEG, PGA, PLA, polycaprolactone or a lycine-derived urethane may be used. In addition, these adhesives may be made in two components such that one component is adherent to the foam and the second injected in vivo. Also, these two component adhesives may be injected simultaneously to mix in vivo to prevent fouling of injection tubes.

Figure 4:
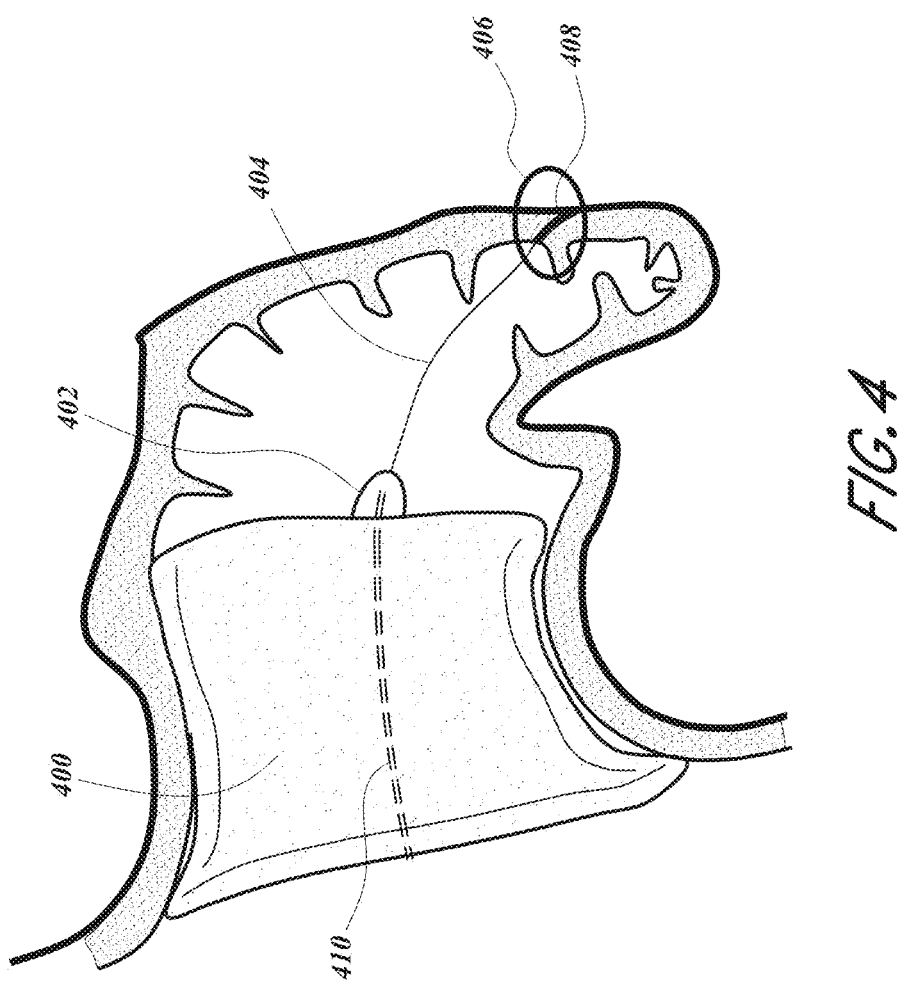
FIG. 4 shows a left atrial appendage with foam embodiment and distal anchor in place.
Figure 5:
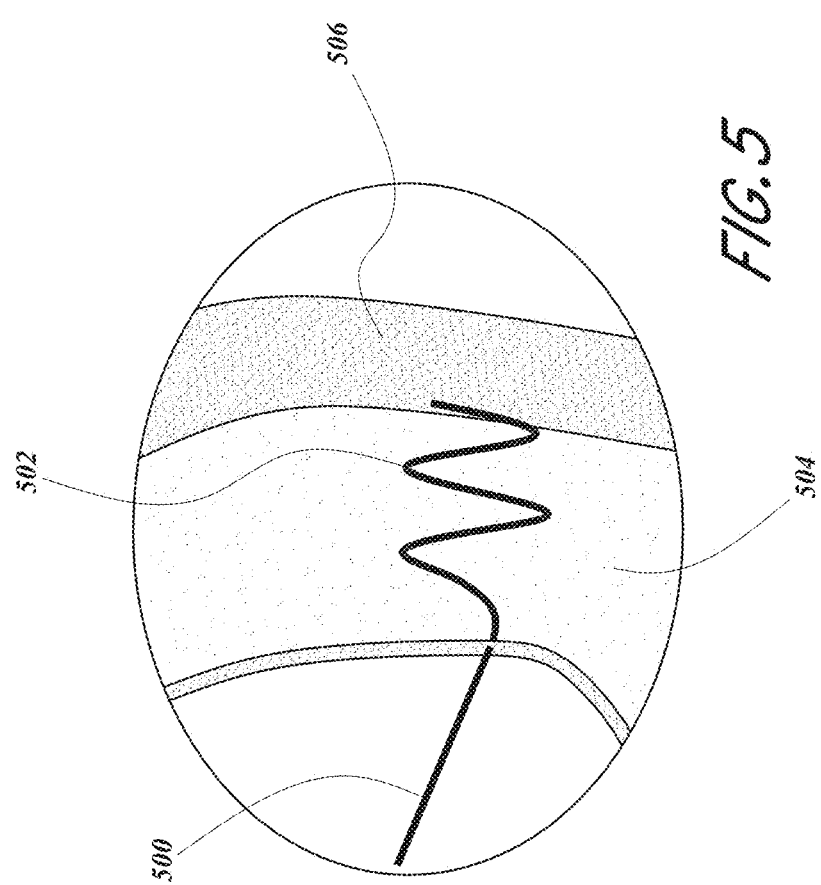
FIG. 5 shows a screw anchor.

An alternative anchoring means for plug 400 is one or two or more distal anchors as shown in FIG. 4. Wire 404 is passed through the center lumen 410 into the LAA and attached to the distal wall of the LAA. In this case, a screw wire 408 is threaded into the wall of the LAA 406. A closer detail of this is seen in FIG. 5 as screw 502 is shown embedded into the LAA wall 504 but not all the way through the epicardial surface 506.

Additional means of anchoring include the use of a plurality of hooks or barbs or graspers to grab the distal wall and baskets, mallecots, distal foam plugs and Nitinol wire birds nests that open within the LAA and push outward on the wall or engage the protrusions of the LAA. It may be desirable to place the plug then engage the anchor as a secondary step. One such embodiment could include a multitude of nitinol wires with a ball or catch welded proximal to the anchor tip. These could be gathered with the delivery catheter then released when the ideal plug position has been confirmed.

Figure 6:
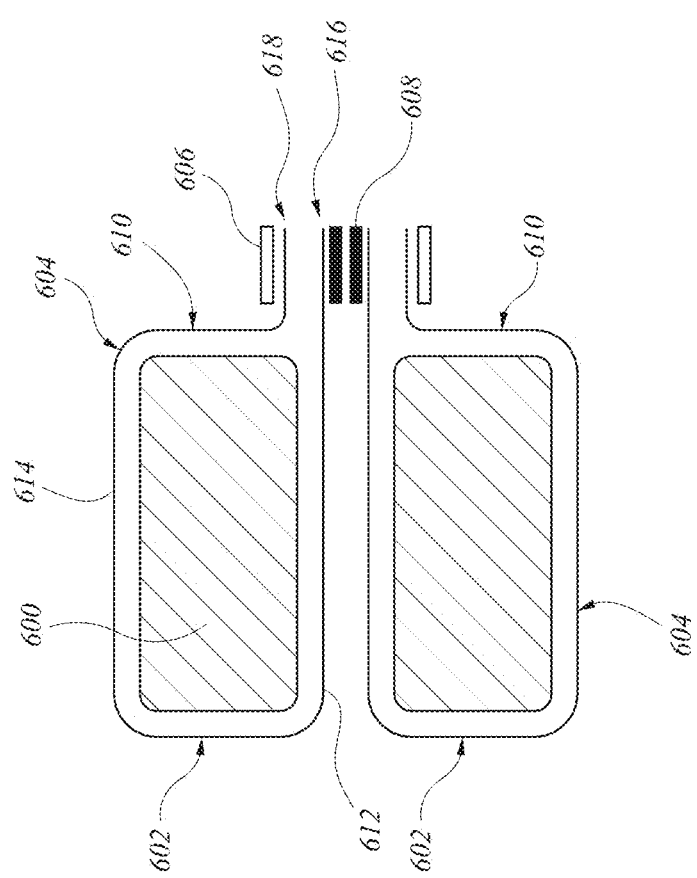
FIG. 6 shows a longitudinal cross section of a foam plug embodiment.
Figure 7:
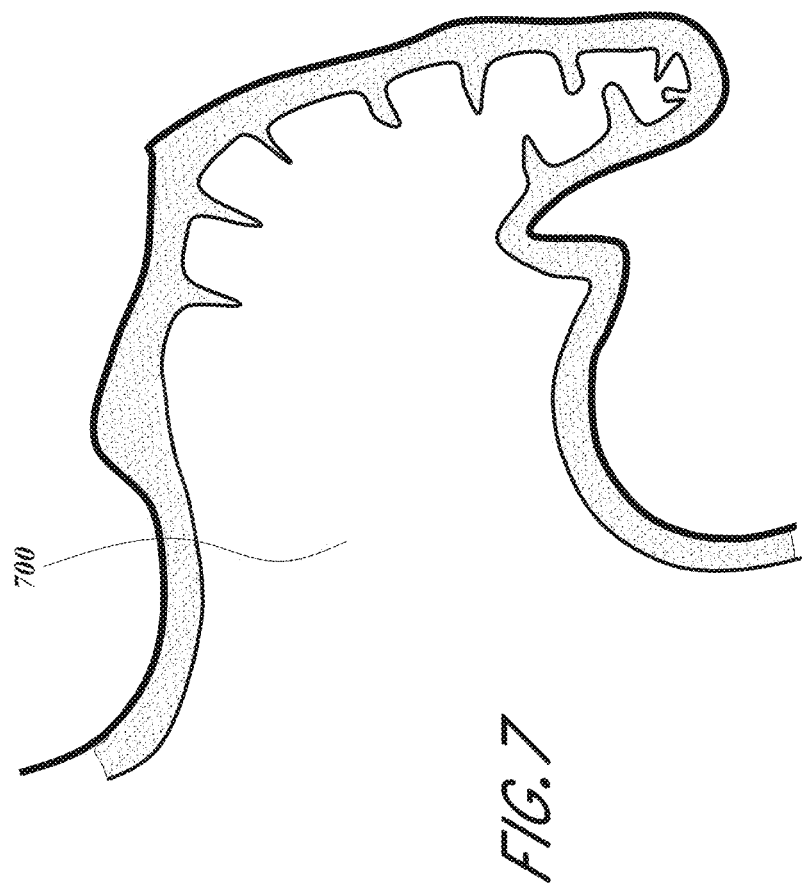
FIG. 7 shows an LAA cross section.
Figure 9:
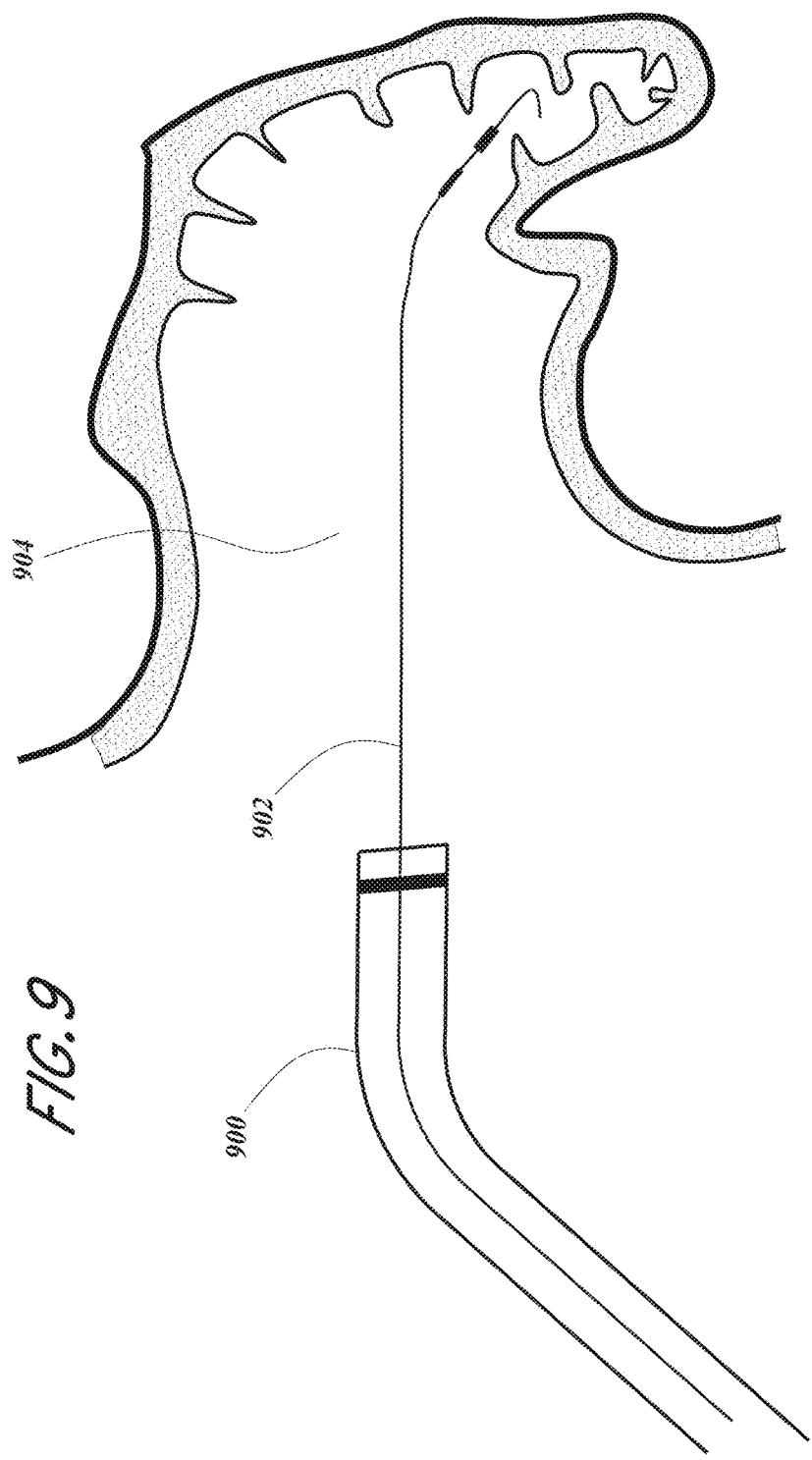
FIG. 9 is an illustration as in FIG. 8, with a guidewire placed within the left atrial appendage.
Figure 10:
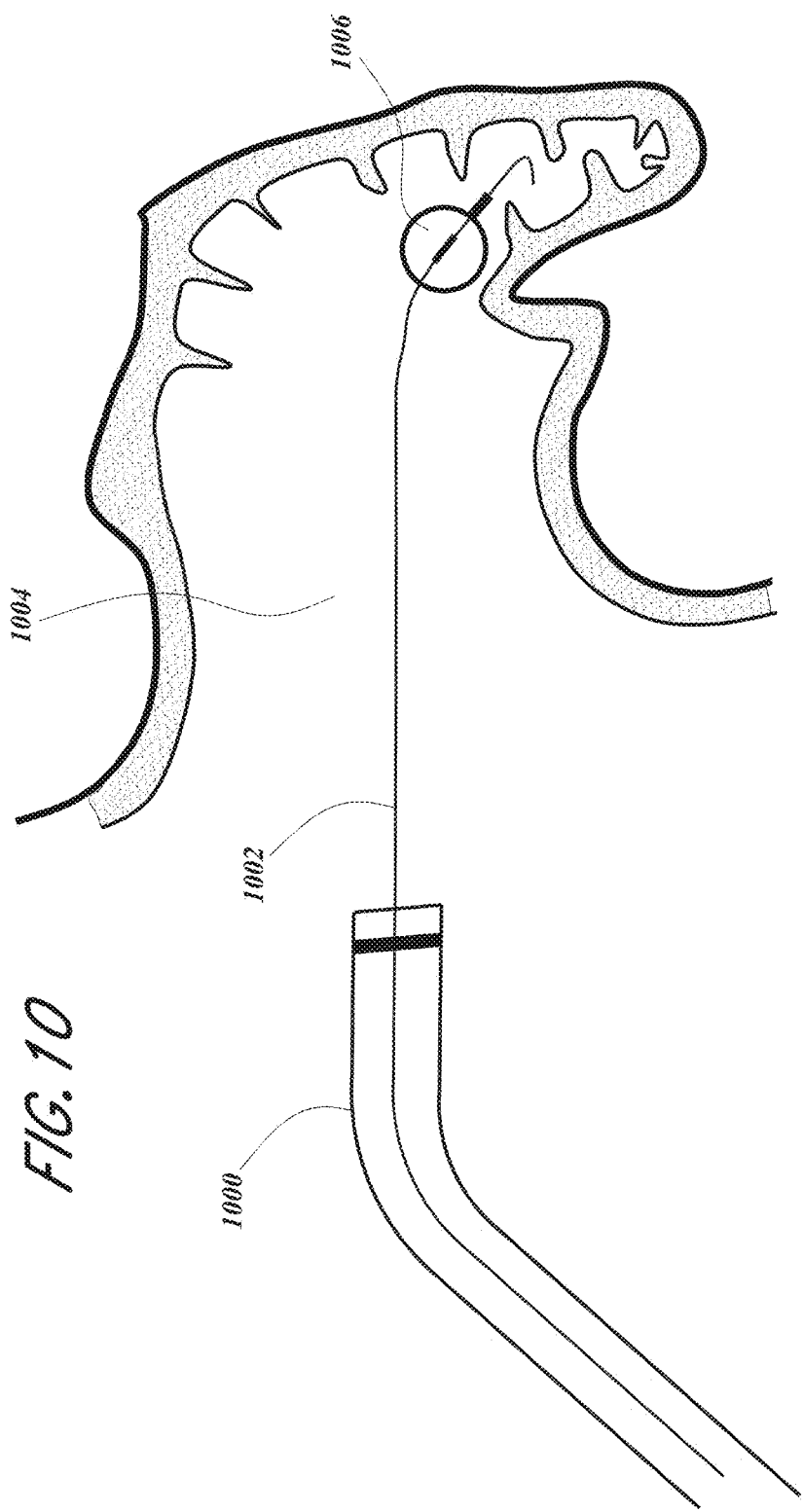
FIG. 10 is an illustration as in FIG. 9, with an inflatable balloon at the distal region of the guidewire positioned within the left atrial appendage.
Figure 11:
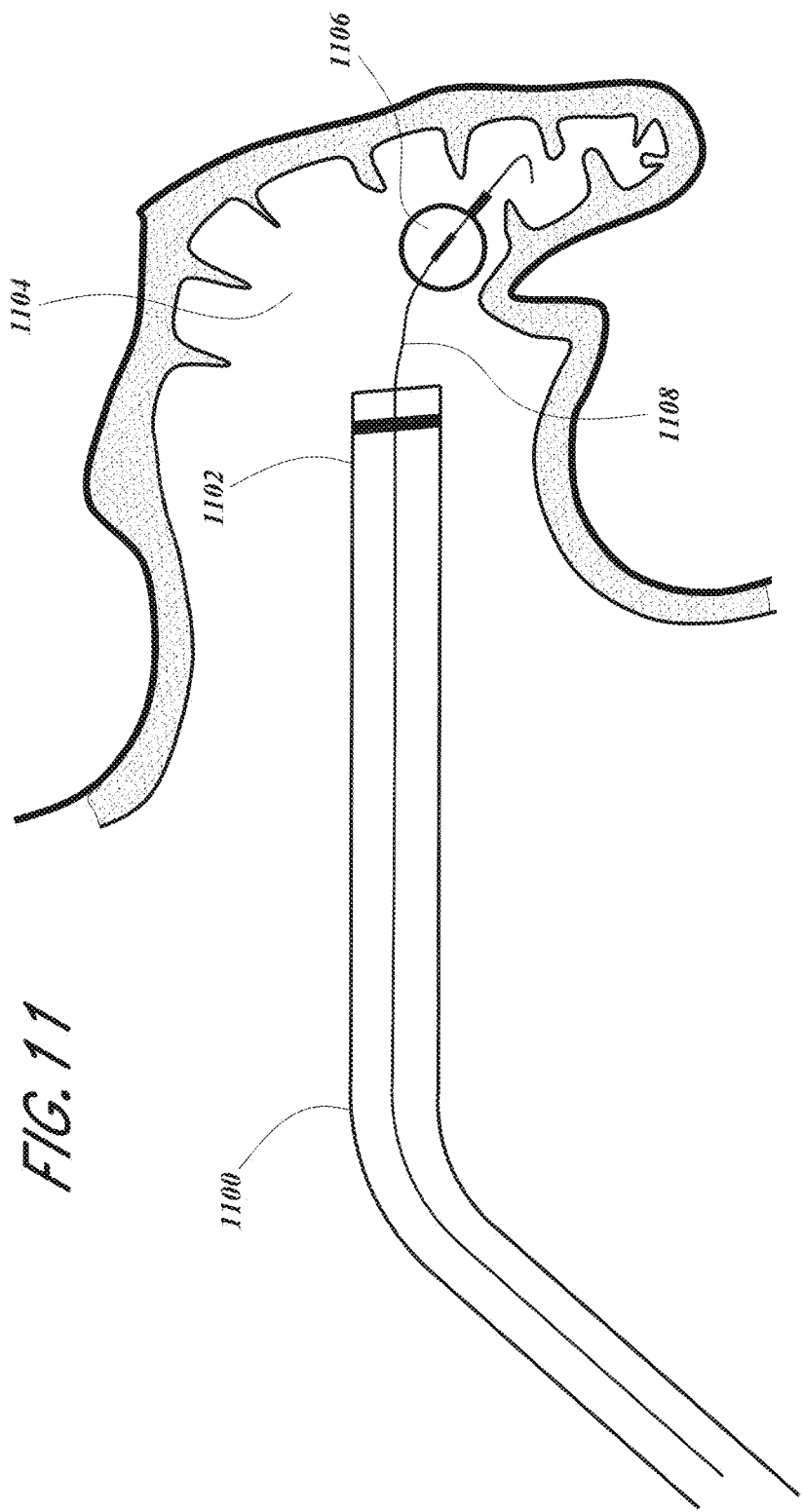
FIG. 11 is an illustration as in FIG. 10, with the guide catheter advanced distally along the guidewire and into the left atrial appendage.

A cross section of one embodiment is shown in FIG. 6 with foam plug 600 and the left atrium face 602 and the LAA face 610. The ePTFE material 604 encapsulates the foam plug 600 and its open ends are connected with an attachment structure such as a wire, suture or tubular crimp 606 over an inner tube 608. The inner tube 608 may be made of an implant grade stainless steel such as 304 or 316 grades or a cobalt-chromium alloy such as MP35n and the crimp 606 may be made of annealed 304 or 316 stainless steel or a cobalt-chromium alloy such as MP35n. This crimp also serves as an element which can be snared should the device need to be removed.

Referring to FIG. 6, the tubular ePTFE layer 604 extends along an inner layer 612 which lines the guidewire lumen, and everts out around the left atrial face 602 to form outer layer 614. A first end 616 of inner layer 612 is disposed concentrically within a second end 618 of outer layer 614. The first end 616 and second end 618 are clamped between inner tube 608 and outer crimp 606. In this manner, the implant can be encapsulated in a manner that presents a seamless left atrial face 602, and preserves the integrity of the guidewire lumen with inner tube 608.

Placement of the device is shown in FIG. 7 through 15. To close the left atrial appendage, the left atrium (LA) must first be accessed from the venous system. One approach is to use a Brockenbrough-style needle to puncture the atrial septum to access the LA from the right atrium (RA). The basic needle-puncture technique is performed obtaining venous access typically via the right femoral vein. A Mullins sheath and dilator are then tracked over a 0.025" or 0.032" guide wire previously placed in the superior vena cava (SVC). Fluoroscopic and echocardiographic imaging, such as transesophageal echo (TEE) or intracardiac echo (ICE), are typically utilized. If echo is not utilized, it is common to also place a pigtail catheter in the aortic root to define the location of the aortic valve, a step not necessary when using echo.

Once the Mullins sheath and dilator are in the SVC, the guide wire is removed and a trans-septal needle is placed through the dilator. The needle contains a stylette to prevent skiving off of polymeric material from the dilator lumen as it traverses to the tip. Once the needle is near the dilator tip, the stylette is removed and the needle is connected to a manifold and flushed. The Mullins sheath/dilator set and the needle (positioned within the dilator tip) are retracted into the SVC toward the RA as a unit. As the system is withdrawn down the wall of the SVC into the RA and positioned in the fossa ovale, the preferred puncture location.

Once proper position in the fossa ovale is observed, the needle is advanced across the fossa ovale into the LA. Successful trans-septal puncture can be confirmed by echo, pressure measurement, $O_2$ saturation and contrast injection. Once the needle position is confirmed to be positioned in the LA, the sheath and dilator can be advanced over it into the LA. In some cases, the user will first pass a guide wire through the needle into the LA and into an upper pulmonary vein (typically the left) prior to crossing. Alternative options include the use of radiofrequency trans-septal needles, which are useful for crossing very thick or hypertrophic septa, or the use of a safety wire placed through the needle and utilized for the initial puncture.

Figure 14:
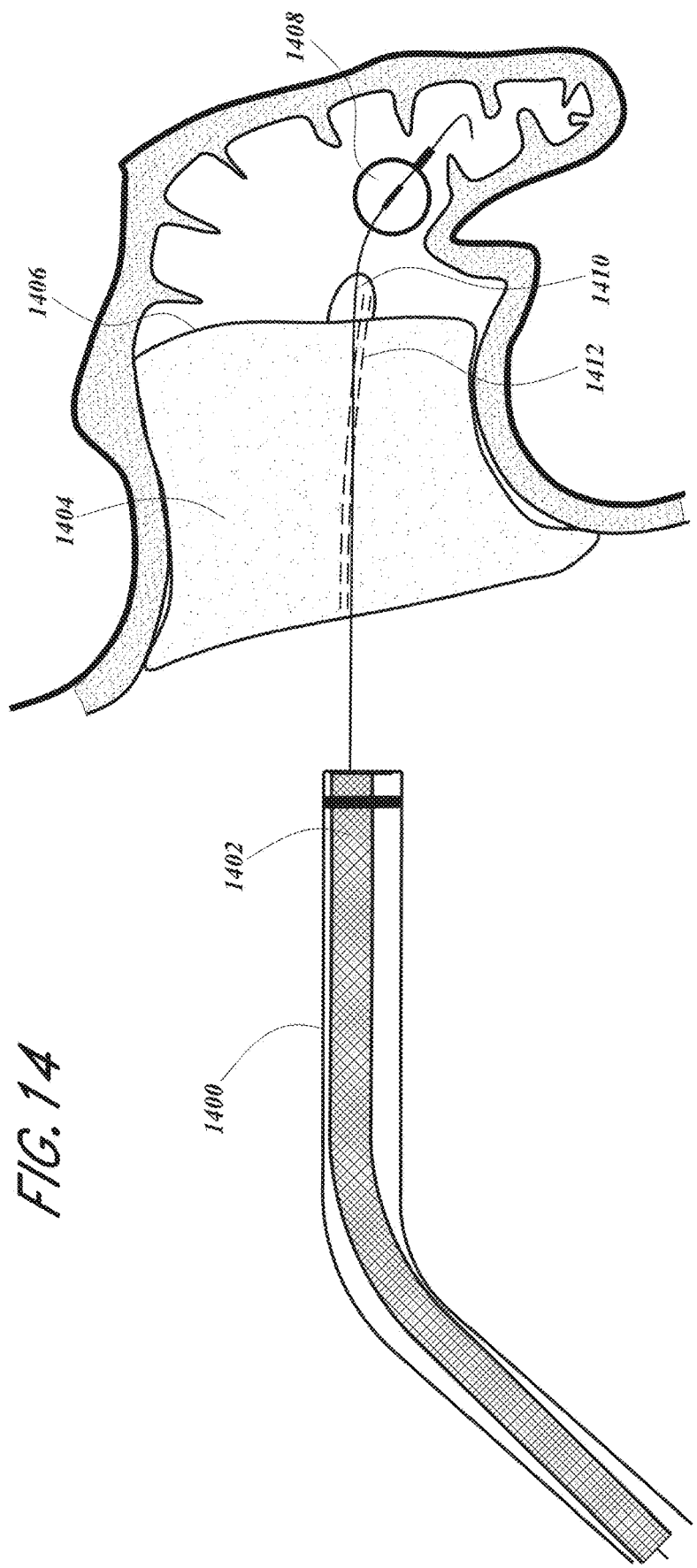
FIG. 14 is an illustration as in FIG. 13, with the occlusion device fully deployed within the left atrial appendage.
Figure 15:
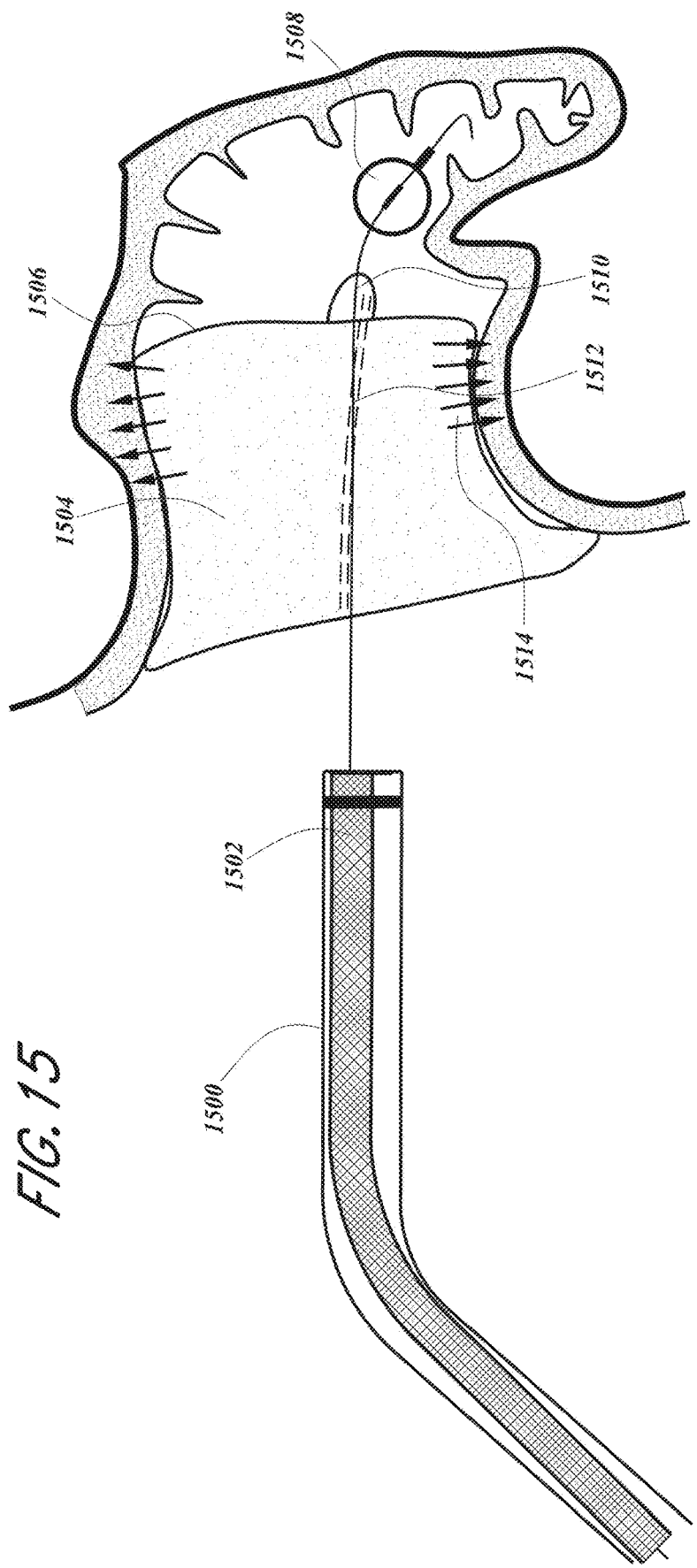
FIG. 15 is an illustration as in FIG. 14, showing the deployment of adhesives or other anchoring structures to retain the occlusion device within the left atrial appendage.

Referring to FIGS. 8 through 15, a guide catheter 802 is placed through the femoral vein into the right atrium of the heart and across the intra-atrial septum into the left atrium as described above and positioned near the LAA ostium 804. A guidewire 902 usually of 0.035" diameter is placed through guide catheter 900 and into the LAA 904. This guidewire 1002 may have attached to its distal end a balloon 1006 which is inflated in the LAA and serves as a bumper to prevent guide catheter 1100 from perforating the wall of the LAA. The guide catheter 1100 is then advanced over the guide wire 1108 into the LAA 1104. A radiopaque marker 1102 is used to guide catheter placement under fluoroscopy. The foam plug 1204 is then pushed through the guide catheter 1200 with pusher 1202 and is shown exiting the guide catheter 1300 slowly in FIG. 13 until it is fully deployed as shown in FIG. 14. The foam plug 1404 position may then be adjusted in place using the distal balloon 1408 and the guide catheter 1400, sliding the foam plug proximally by pulling on the balloon 1408 through shaft 1412 or sliding it distally by pushing guide catheter 1400 distally.

The guide wire may also contain a pressure sensor within it such that sealing of the LAA is monitored and confirmation of a sufficient seal is made. Once the user is happy with the placement, the adhesive 1514 may be injected and/or mechanical anchors be deployed anchoring the plug to the wall. The guide wire balloon 1508 is deflated, after which the guide wire. In an alternative embodiment, a binary adhesive system can be used where one component of the binary system is bonded to the outer surface of the skin covering the foam plug. The second component can be injected at the interface between foam plug and the wall of the LAA such that bonding happens only at the interface minimizing the risk of adhesive embolization.

Figure 12:
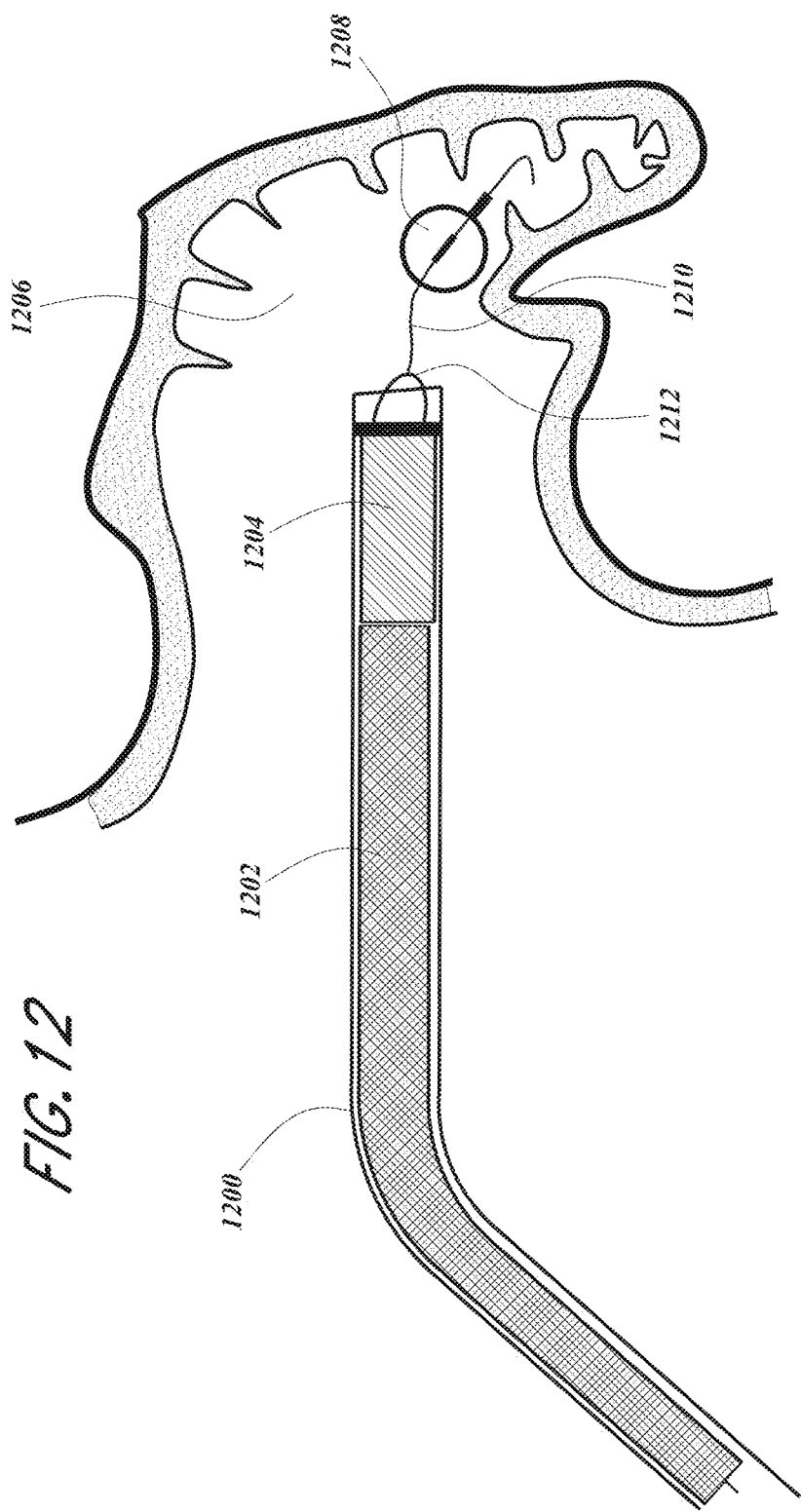
FIG. 12 is an illustration as in FIG. 11, showing the occlusion device and pusher positioned within the guide catheter.
Figure 13:
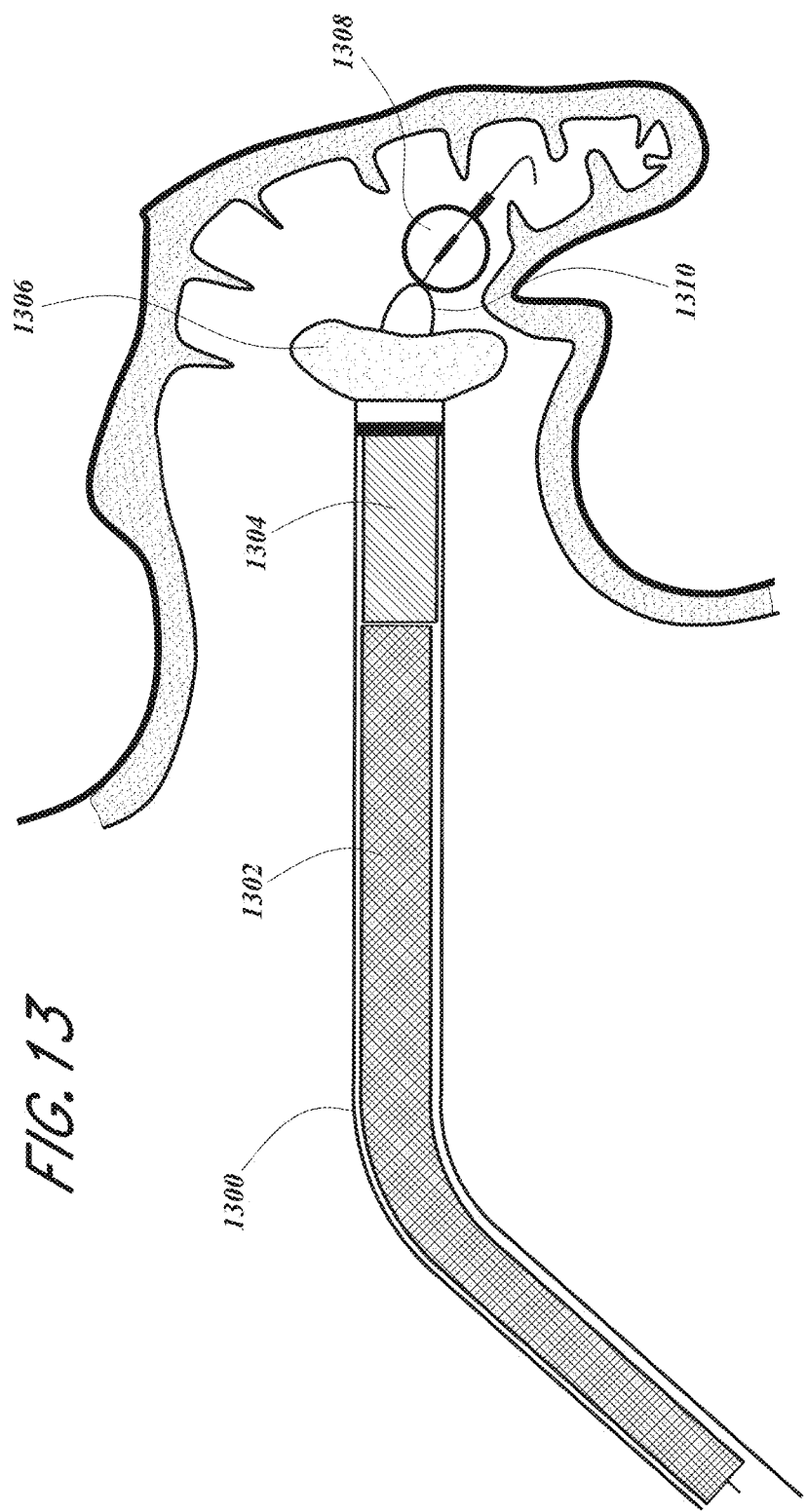
FIG. 13 is an illustration as in FIG. 12, showing the occlusion device partially deployed exiting the guide catheter.

An alternative to pushing the plug through the entire length of the guide catheter is that the plug 1204 may be initially located at the distal end of the guide catheter 1200 as shown in FIG. 12. The guidewire 1210 passes through the center of the plug 1204 and in this mode, the pusher 1202 only needs to push the plug a short ways to deploy it into the LAA.

For alternative anchors, they may be deployed, the shafts disconnected and removed. Disconnection mechanisms may be any of several types, such as threaded, electrolytic detachment, or others known in the art.

Figure 16:
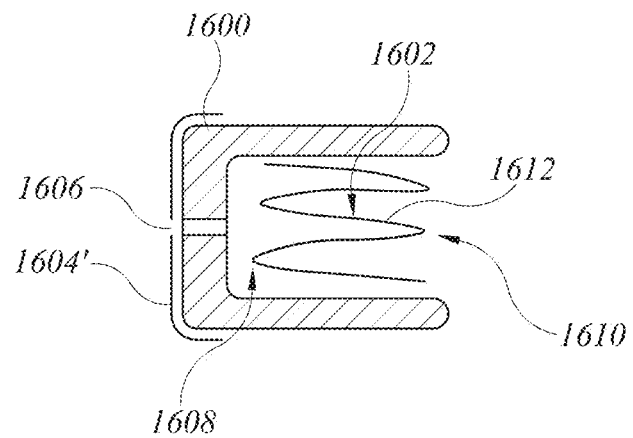
FIG. 16 shows a plug occlusive device in longitudinal cross section using metal and foam.

Alternative plug concepts include a combination of foam and metal implant as shown in FIG. 16. The foam 1600 is designed to provide ingrowth of tissue and also to provide a cushion of the metal stent 1602 onto the tissue of the LAA. The proximal face 1604' of the plug is covered in ePTFE, polyester or another thromboresistant tissue scaffold material to facilitate sealing with the desired pore size to encourage overgrowth. Stent 1602 could be made of Nitinol to enable it to pack into a 10, 12, 14, 16, 18 or 20F delivery catheter and expand to its desired diameter. It could be braided, laser cut or wire formed. Any of a variety of stent wall patterns may be utilized, depending upon the desired performance. The stent may be a balloon expandable stent, or self-expandable stent as are understood in the art. In the illustrated embodiment, a self-expandable stent 1602 comprises a plurality of proximal apexes 1608 and distal apexes 1610 connected by a plurality of zig zag struts 1612. A hole 1606 allows passage of the guidewire for delivery. This design may be advantageous in that the expansion force exerted by the plug on the LAA can be controlled separately from the foam characteristics. Also, it may be easier to pack this concept into a smaller geometry.

Alternatively, the foam plug may be constructed of 2 foams. One denser core to provide force and an outer softer foam to engage the tissue irregularities. The softer foam could also be located on the proximal and/or distal ends to facilitate retrieval.

Figure 17:
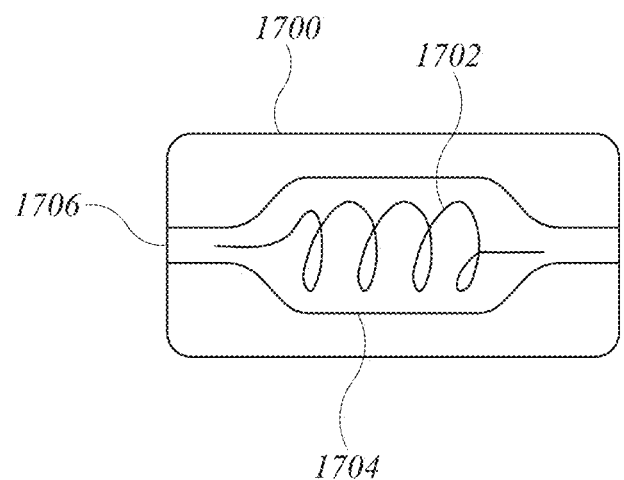
FIG. 17 shows a plug using metal coils and foam.

Another means of adding stiffness to the foam plug is shown in FIG. 17 where a cavity 1704 in the foam plug 1700 is made and a coil of wire 1702 may be advanced from the guide catheter at the proximal end 1706 into the cavity 1704. As the wire enters the cavity, it expands to its predetermined size and exerts force on the foam radially outwards. The type and amount of wire may be determined in vivo using x-ray guidance to examine the radial expansion of the foam into the LAA.

Instead of wires as shown in FIG. 17, a balloon may be passed into the foam and inflated to provide radial force while the outer foam serves to engage the tissue irregularities and tissue ingrowth. Following inflation, the balloon may be detached from a deployment catheter and the deployment catheter withdrawn. The balloon is preferably provided with a valve, to prevent the escape of inflation media. Inflation media may be any of a variety of media which is convertible between a first, flowable state and a second, hardened state such as by cross linking or polymerization in situ.

Figure 18:
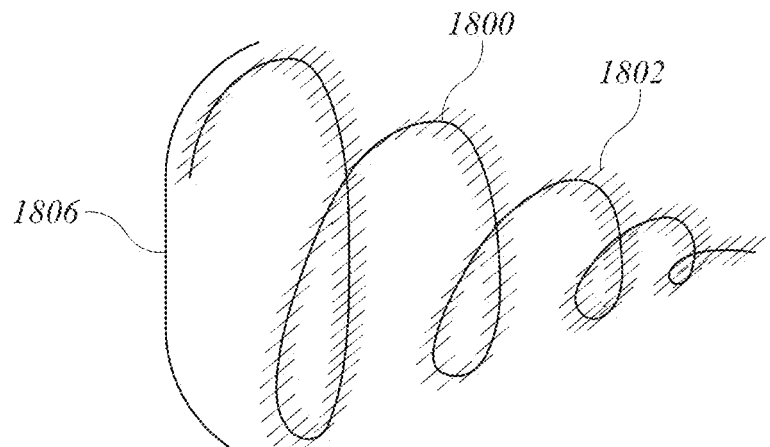
FIG. 18 shows a plug using a single metal coil.

Another LAA plug is shown in FIG. 18 as a spring like implant wire 1800 that is covered with foam 1802 to encourage ingrowth. The proximal face of the implant is covered with a sheet of ePTFE or other tissue scaffolding material. This implant may be stretched out for delivery and released in place.

Rather than using a foam, a low porosity outer bag without perforations could be placed in the LAA and then filled with a substance to provide the radial expansion. This substance may be a hydrogel, cellulose or polyvinylacetate.

Figure 19:
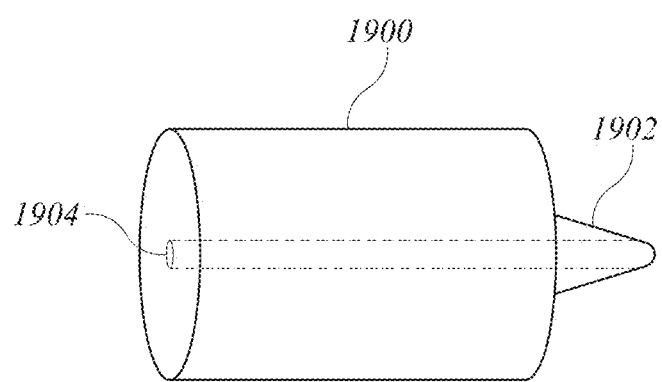
FIG. 19 shows a plug with a dilating distal tip.

Rather than requiring the use of a separate dilation device to cross the septum, the distal crimp element 1902 may be formed in a tapered manner such that it extends from the distal end of the catheter 1200 and serves as a dilating tip to dilate the opening in the septum as the catheter is advanced. See FIG. 19.

Figure 22:
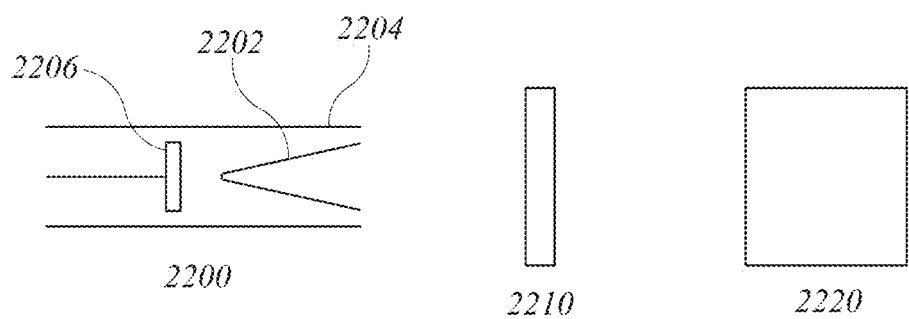
FIG. 22 shows the delivery of an expanding foam system.

An alternative plug design uses a foam such as cellulose sponge material that is compacted and dehydrated such that it can be packed into the guide catheter. This foam material 2202 may be packed into the guide catheter as shown in FIG. 22. The foam plug 2202 is then advanced from the distal end of the guide catheter 2204 with a plunger 2206 into the LAA. The plug exits the guide catheter and opens to a disc shape 2210. As the foam absorbs fluid in the blood, its length expands to form a cylinder 2220 filling the LAA. Expansion ratios for compressed cellulose materials may be as high as 17:1, expanded to compressed length.

Figure 23:
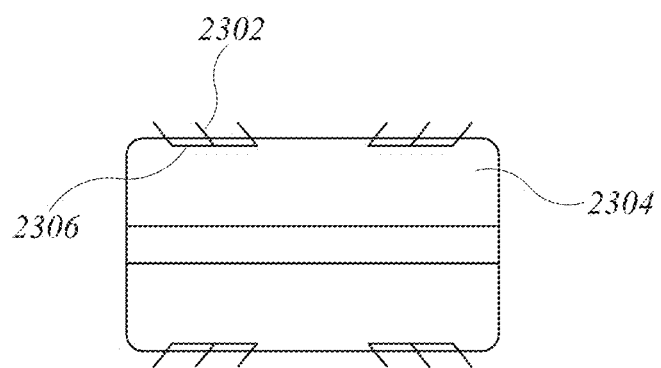
FIG. 23 shows a plug with barbs.

It may be advantageous to use small barbs 2302 in FIG. 23 to further engage the plug 2204 into the LAA. Barbs may be unidirectional or bidirectional to resist movement in either the proximal or distal direction. These barbs are embedded into the foam plug and may be 0.1 to 1 mm in height. It may be desirable to place the plug then engage the barbs as a secondary step. One such embodiment could include a multitude of nitinol barb wires with a ball or catch welded proximal to the barb tip. These could be gathered with the delivery catheter within a sleeve or suture then released when the ideal plug position has been confirmed.

Figure 24:
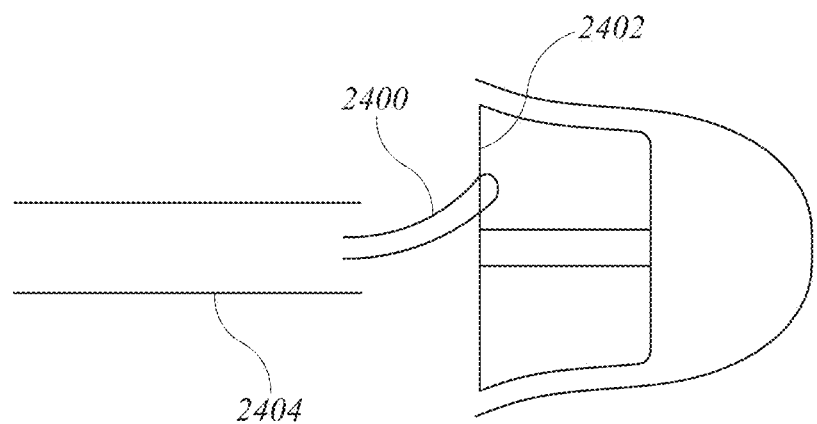
FIG. 24 shows a plug with a retrieval suture attachment.

One means of removing a device that is not functioning properly is to releasably attach a retrieval suture 2400 to the implant, such as to the proximal cap 2402 which also passes proximally throughout the entire length of the guide catheter 2404 in FIG. 24. If the device is to be removed, pulling on both ends of the suture 2400 will pull the outer covering into the guide catheter 2404 which can then be removed from the patient. If the device is properly placed, the suture 2400 may be cut and removed leaving the plug in place.

Deployment of the occlusion device has been discussed primarily in the context of a transvascular access. However, implants of the present invention may alternatively be deployed via direct surgical access, or various minimally invasive access pathways (e.g. jugular vein). For example, the area overlying the xiphoid and adjacent costal cartilage may be prepared and draped using standard techniques. A local anesthetic may be administered and skin incision may be made, typically about 2 cm in length. The percutaneous penetration passes beneath the costal cartilage, and a sheath may be introduced into the pericardial space. The pericardial space may be irrigated with saline, preferably with a saline-lidocaine solution to provide additional anesthesia and reduce the risk of irritating the heart. The occlusion device may thereafter be introduced through the sheath, and through an access pathway created through the wall of the LAA. Closure of the wall and access pathway may thereafter be accomplished using techniques understood in the art.

Depending upon the desired clinical performance, any of the LAA occlusion devices of the present invention may be provided with a drug or other bioactive agent, which may be injected via the deployment catheter, or impregnated within the open cell foam or coated on the implant. The bioactive agent may be eluted or otherwise released from the implant into the adjacent tissue over a delivery time period appropriate for the particular agent as is understood in the art.

Useful bioactive agents can include those that modulate thrombosis, those that encourage cellular ingrowth, through-growth, and endothelialization, and potentially those that resist infection. For example, agents that may promote endothelial, smooth muscle, fibroblast, and/or other cellular growth into the implant including collagen (Type I or II), heparin, a combination of collagen and heparin, extracellular matrix (ECM), fibronectin, laminin, vitronectin, peptides or other biological molecules that serve as chemoattractants, molecules MCP-1, VEGF, FGF-2 and TGF-beta, recombinant human growth factors, and/or plasma treatment with various gases.

Anti-thrombotics can typically be separated into anti-coagulants and antiplatelet agents. Anti-Coagulants include inhibitors of factor(s) within the coagulation cascade an include heparin, heparin fragments and fractions as well as inhibitors of thrombin including hirudin, hirudin derivatives, dabigatran, argatroban and bivalrudin and Factor X inhibitors such as low molecular weight heparin, rivaroxaban, apixaban.

Antiplatelet agents include GP 2b/3a inhibitors such as epifibitide, and abciximab, ADP Receptor agonists (P2/Y12) including thienopyridines such as ticlopidine, clopidogrel, prasugrel and tacagrelor and aspirin. Other agents include lytic agents, including urokinase and streptokinase, their homologs, analogs, fragments, derivatives and pharmaceutical salts thereof and prostaglandin inhibitors.

Antibiotic agents can include, but are not limited to penicillins, cephalosportins, vancomycins, aminoglycosides, quinolonges, polymyxins, erythromycins, tetracyclines, chloraphenicols, clindamycins, lincomycins, sulfonamides, their homologs, analogs, derivatives, pharmaceutical salts and combinations thereof.

Figure 25A:
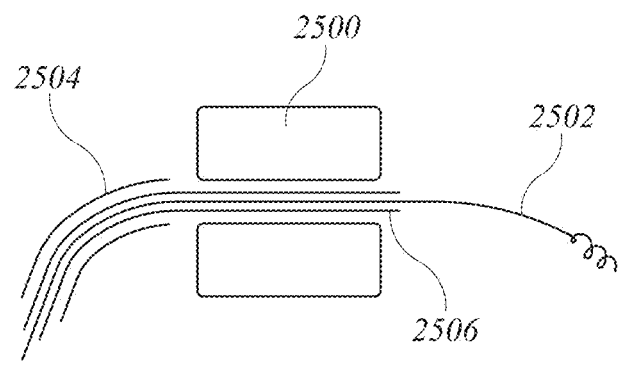
FIGS. 25A and 25B show a distal anchoring system.
Figure 25B:
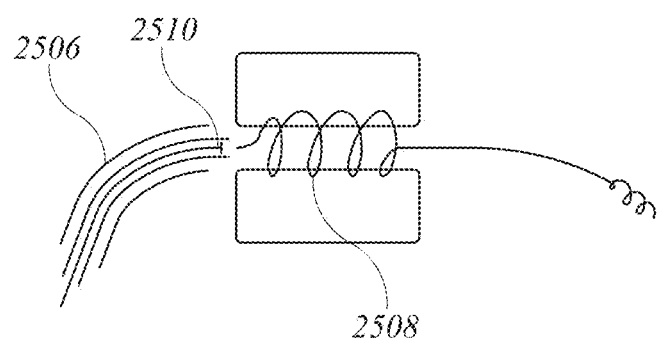

Another means of anchoring is shown in FIG. 25A where the foam plug 2500 is placed in the LAA. The distal screw lead 2502 is advanced and screwed into the LAA wall. Guide 2506 is pulled proximally as shown in FIG. 25B. When this guide 2506 is pulled back, the screw lead wire, made of Nitinol, bunches up into a "birds nest" 2508 or forms a coil inside the foam plug 2500. The screw lead wire 2502 is pushed distally from the guide catheter 2504 with a pusher 2510 and continues to bunch up into the foam. The catheter system 2504, 2506 and 2510 are then removed.

Figure 26:
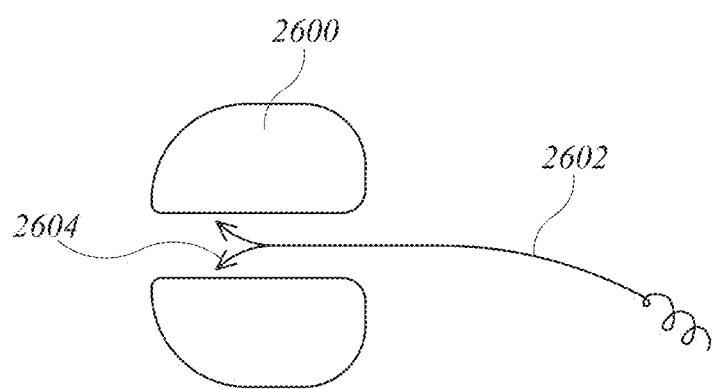
FIG. 26 shows an alternative distal anchoring system.

Another means of anchoring the distal anchor element to the foam is shown in FIG. 26. Two barbed leads 2604 are attached to anchor 2602 such that when advanced into place in the foam plug 2600, the barbs 2604 dig into the foam plug.

Biologic agents as outlined above maybe be added to the implant 204 and may be injected through the delivery catheter into the space between the proximal cap 206 and the foam plug 204. This may serve as a reservoir to minimize thrombus formation during the initial implantation and reduce the need for systemic anticoagulation following device implantation.

An electronic pressure sensor may be embedded into the proximal end of the foam plug which may be used to transmit LA pressure to a remote receiver outside the body for the monitoring of LA pressure which is useful to monitor cardiac function. In addition, a cardiac pacer or defibrillator may be embedded into the foam plug and attached electrically to the distal anchor. A drug delivery reservoir may be embedded with connection to the LA for controlled delivery of biologic agents as outlined above.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It will be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

What is claimed is:

1. A left atrial appendage occlusion device, comprising:
an expandable body having an open cell foam proximal, occlusive end for facing a left atrium following implantation of the device in a left atrial appendage, a distal end for facing into the left atrial appendage following implantation of the device in the left atrial appendage, and a cylindrical open cell foam sidewall, wherein the distal end of the expandable body comprises a distal opening for facing into the left atrial appendage following implantation and the open cell foam sidewall forms the distal opening;
a self-expandable stent carried within the expandable body wherein the foam sidewall extends distally linearly beyond the stent at least in a deployed configuration such that following implantation the foam sidewall forms a distal-most end of the device and provides a cushion between the stent and the left atrial appendage, the stent comprising a proximal end positioned within the expandable body distal to the proximal, occlusive end of the expandable body and a plurality of zig-zag struts defining a plurality of apexes including a plurality of distal apexes formed by vertices of adjacent pairs of the zig-zag struts at a distal-most end of the stent; and
a thromboresistent covering on at least a portion of the expandable body.

2. The left atrial appendage occlusion device of claim 1, wherein the thromboresistent covering comprises a mesh.

3. The left atrial appendage occlusion device of claim 1, wherein the thromboresistent covering comprises ePTFE.

4. The left atrial appendage occlusion device of claim 1, wherein the thromboresistent covering is on at least a portion of the proximal end of the expandable body.

5. The left atrial appendage occlusion device of claim 4, wherein the thromboresistent covering on at least a portion of the proximal end of the expandable body comprises a mesh.

6. The left atrial appendage occlusion device of claim 1, wherein the stent comprises a plurality of proximal apexes.

7. The left atrial appendage occlusion device of claim 1, comprising at least one tissue ingrowth surface on the sidewall of the body.

8. The left atrial appendage occlusion device of claim 1, further comprising a suture releasably attached to the proximal end of the expandable body.

9. The left atrial appendage occlusion device of claim 1, wherein the expandable body is cylindrical in shape in an unconstrained expansion.

10. The left atrial appendage occlusion device of claim 1, further comprising at least one anchor.

11. The left atrial appendage occlusion device of claim 10, wherein the at least one anchor comprises a tissue penetrating element.

12. The left atrial appendage occlusion device of claim 1, further comprising at least one radiopaque marker.

13. The left atrial appendage occlusion device of claim 12, wherein the at least one radiopaque marker comprises a radiopaque thread.

14. The left atrial appendage occlusion device of claim 1, wherein the expandable body comprises polycarbonate-polyurethane urea foam.

15. The left atrial appendage occlusion device of claim 1, wherein the expandable body can be compressed within a delivery catheter having an inside diameter of no more than about 20F and the expandable body can self-expand to a diameter of at least about 25 mm when released from the delivery catheter.

16. The left atrial appendage occlusion device of claim 1, wherein the expandable body is coated with a material to enhance thromboresistance.

* * * * *